United States Patent
Lee et al.

(10) Patent No.: US 11,419,573 B2
(45) Date of Patent: Aug. 23, 2022

(54) METHOD FOR OUTPUTTING SPEED OF OBJECT AND ULTRASONIC DIAGNOSIS DEVICE THEREFOR

(71) Applicant: SAMSUNG MEDISON CO., LTD., Hongcheon-gun (KR)

(72) Inventors: Seung-heun Lee, Seongnam-si (KR); Kang-sik Kim, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 901 days.

(21) Appl. No.: 16/072,416

(22) PCT Filed: Mar. 9, 2016

(86) PCT No.: PCT/KR2016/002317
§ 371 (c)(1),
(2) Date: Jul. 24, 2018

(87) PCT Pub. No.: WO2017/135500
PCT Pub. Date: Aug. 10, 2017

(65) Prior Publication Data
US 2019/0029636 A1    Jan. 31, 2019

(30) Foreign Application Priority Data
Feb. 2, 2016  (KR) .................. 10-2016-0012902

(51) Int. Cl.
*A61B 8/00*   (2006.01)
*A61B 8/06*   (2006.01)
(Continued)

(52) U.S. Cl.
CPC .............. *A61B 8/06* (2013.01); *A61B 5/0044* (2013.01); *A61B 5/7257* (2013.01); *A61B 5/748* (2013.01);
(Continued)

(58) Field of Classification Search
CPC ... A61B 5/0044; A61B 5/1172; A61B 5/7257; A61B 5/7405; A61B 5/748; A61B 8/00;
(Continued)

(56) References Cited

U.S. PATENT DOCUMENTS 4,966,153 A   10/1990 Nakamura et al.
5,509,416 A    4/1996 Wilmott
(Continued)

FOREIGN PATENT DOCUMENTS

CN    1440726 A    9/2003
CN    1549933 A   11/2004
(Continued)

OTHER PUBLICATIONS

Communication dated Aug. 4, 2020, issued by the State Intellectual Property Office of P.R. China in counterpart Chinese Application No. 201680080895.1.
(Continued)

*Primary Examiner* — Christopher L Cook
(74) *Attorney, Agent, or Firm* — Sughrue Mion, PLLC

(57) ABSTRACT

Provided is a method of outputting a velocity of an object, the method including: transmitting an ultrasound signal to an object and receiving an ultrasound echo signal returned from the object; determining a velocity of the object based on the ultrasound echo signal; displaying a spectral Doppler image showing velocities of the object over time; receiving user inputs of selecting an interval within a range of the velocities of the object shown in the spectral Doppler image and adjusting an output volume of an audible sound corresponding to velocities in the selected interval; and outputting, based on the adjusted output volume of the audible sound, an audible sound representing the velocities of the object over time.

14 Claims, 15 Drawing Sheets

(51) Int. Cl.
    *A61B 8/14*         (2006.01)
    *A61B 8/08*         (2006.01)
    *A61B 5/00*         (2006.01)
    *G06F 3/01*         (2006.01)
    *G01S 15/89*        (2006.01)
    *A61B 5/1172*     (2016.01)

(52) U.S. Cl.
    CPC .......... *A61B 8/00* (2013.01); *A61B 8/08* (2013.01); *A61B 8/0891* (2013.01); *A61B 8/14* (2013.01); *A61B 8/467* (2013.01); *A61B 8/488* (2013.01); *G01S 15/8979* (2013.01); *G06F 3/017* (2013.01); *A61B 5/1172* (2013.01); *A61B 5/7405* (2013.01)

(58) Field of Classification Search
    CPC .......... A61B 8/06; A61B 8/08; A61B 8/0891; A61B 8/14; A61B 8/467; A61B 8/488; G01S 15/8979; G06F 3/017; G06F 3/033; G06F 3/04847; G06F 3/0488
    See application file for complete search history.

(56) References Cited

U.S. PATENT DOCUMENTS

| | | | | |
|---|---|---|---|---|
| 5,640,960 | A * | 6/1997 | Jones | A61B 8/0866 |
| | | | | 600/453 |
| 5,871,447 | A * | 2/1999 | Ramamurthy | A61B 8/08 |
| | | | | 600/443 |
| 6,390,983 | B1 * | 5/2002 | Mo | G01S 15/8981 |
| | | | | 600/453 |
| 6,705,997 | B2 | 3/2004 | Amemiya | |
| 7,513,873 | B2 | 4/2009 | Shifrin | |
| 8,100,832 | B2 | 1/2012 | Kunita | |
| 9,895,138 | B2 | 2/2018 | Sasaki | |
| 10,357,228 | B2 | 7/2019 | Yoon et al. | |
| 10,463,263 | B2 | 11/2019 | Alpert et al. | |
| 2002/0173721 | A1 * | 11/2002 | Grunwald | A61B 8/462 |
| | | | | 600/437 |
| 2003/0045797 | A1 * | 3/2003 | Christopher | G01S 7/52026 |
| | | | | 600/453 |
| 2003/0120286 | A1 * | 6/2003 | Burbank | A61B 17/12 |
| | | | | 606/142 |
| 2008/0215982 | A1 * | 9/2008 | Washburn | A61B 8/08 |
| | | | | 715/722 |
| 2009/0131791 | A1 * | 5/2009 | Clark | G01S 15/8979 |
| | | | | 600/441 |
| 2010/0286521 | A1 * | 11/2010 | Betts | G01S 7/52085 |
| | | | | 600/441 |
| 2012/0059264 | A1 | 3/2012 | Hope Simpson et al. | |
| 2013/0281862 | A1 | 10/2013 | Yoon et al. | |
| 2014/0064519 | A1 * | 3/2014 | Silfvast | H04H 60/04 |
| | | | | 381/119 |
| 2014/0066773 | A1 * | 3/2014 | Takimoto | A61B 8/461 |
| | | | | 600/453 |
| 2014/0281984 | A1 * | 9/2014 | Milne | G06T 11/206 |
| | | | | 715/716 |
| 2016/0081664 | A1 | 3/2016 | Osumi et al. | |
| 2017/0035392 | A1 | 2/2017 | Grunwald et al. | |

FOREIGN PATENT DOCUMENTS

| | | |
|---|---|---|
| CN | 101292880 A | 10/2008 |
| CN | 102421372 A | 4/2012 |
| CN | 102958451 A | 3/2013 |
| CN | 103371847 A | 10/2013 |
| CN | 103635144 A | 3/2014 |
| JP | 2-13449 A | 1/1990 |
| JP | 6-47027 A | 2/1994 |
| JP | 6-61209 U | 8/1994 |
| JP | 7-16227 A | 1/1995 |
| JP | 7-116165 A | 5/1995 |
| JP | 8-166449 A | 6/1996 |
| JP | 4559215 B2 | 10/2010 |
| JP | 2015-091325 A | 5/2015 |
| KR | 10-99332 A | 4/1998 |
| KR | 10-2002-0073400 A | 9/2002 |
| KR | 10-2005-0025557 A | 3/2005 |
| KR | 10-2013-0118199 A | 10/2013 |
| WO | 2014/196570 A1 | 12/2014 |

OTHER PUBLICATIONS

Communication dated Sep. 7, 2020, issued by the European Patent Office in counterpart European Application No. 16889478.0.
Communication dated Sep. 18, 2019 issued by the European Intellectual Property Office in counterpart European Application No. 16889478.0.
Search Report dated Oct. 12, 2016, issued by the International Searching Authority in counterpart International Patent Application No. PCT/KR2016/002317 (PCT/ISA/210).
Written Opinion dated Oct. 12, 2016, issued by the International Searching Authority in counterpart International Patent Application No. PCT/KR2016/002317 (PCT/ISA/237).
Communication dated May 19, 2021, issued by the State Intellectual Property Office of P.R. China in counterpart Chinese Application No. 201680080895.1.
Communication dated Dec. 1, 2021, issued by the National Intellectual Property Administration of P.R. China in counterpart Chinese Application No. 201680080895.1.

* cited by examiner

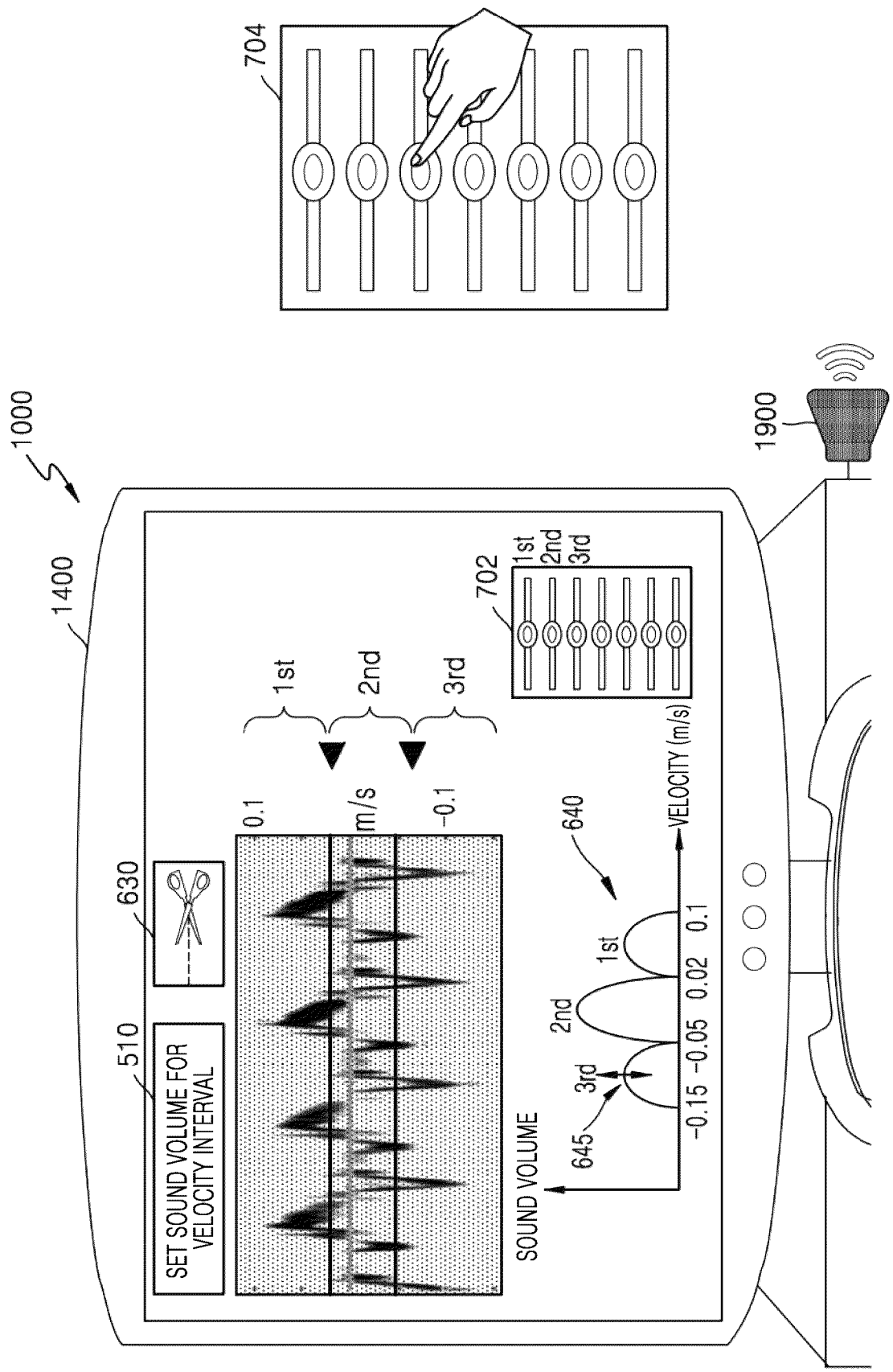

METHOD FOR OUTPUTTING SPEED OF OBJECT AND ULTRASONIC DIAGNOSIS DEVICE THEREFOR

TECHNICAL FIELD

The present disclosure relates to an ultrasound diagnosis apparatus and method for outputting a velocity of an object.

BACKGROUND ART

Ultrasound diagnosis apparatuses transmit ultrasound signals generated by transducers of a probe to an object and receive information about echo signals reflected from the object, thereby obtaining an image of an internal part (e.g., soft tissues or blood flow) of the object. In particular, ultrasound diagnosis apparatuses are used for medical purposes including observing an internal area of an object, detecting foreign substances, and assessing injuries. Such ultrasound diagnosis apparatuses exhibit high stability, display images in real time, and are safe due to a lack of radiation exposure, compared to diagnostic X-ray apparatuses. Therefore, ultrasound diagnosis apparatuses have been widely used together with other types of imaging diagnosis apparatuses.

Furthermore, an ultrasound diagnosis apparatus may use a Doppler effect to measure a speed and a direction of a moving object and output the measured speed and direction of the object. For example, an ultrasound diagnosis apparatus may measure a speed and a direction_of blood flow or a moving muscle within the heart or carotid artery.

When an object moves, a difference between frequencies of an ultrasound signal transmitted to the object and an ultrasound echo signal reflected from the object occurs, and the frequency difference is called a Doppler shift frequency. As the object moves at a higher velocity, a magnitude of a Doppler shift frequency becomes greater. Thus, an ultrasound diagnosis apparatus may determine a velocity of the object based on a magnitude of a calculated Doppler shift frequency.

Furthermore, since a Doppler shift frequency is in a frequency range of an audible sound, the ultrasound diagnosis apparatus may indicate the measured velocity of the object by outputting an audible sound having a calculated Doppler shift frequency.

DESCRIPTION OF EMBODIMENTS

Technical Problem

According to some embodiments, there is provided an ultrasound diagnosis apparatus and method for measuring velocities of an object and outputting detailed information about velocities in an interval selected by a user from among the measured velocities.

In some embodiments, there is provided an ultrasound diagnosis apparatus and method for selectively adjusting an ultrasound Doppler sound signal.

Solution to Problem

According to an aspect of the present disclosure, there is provided a method of outputting a velocity of an object, which includes: transmitting an ultrasound signal to the object and receiving an ultrasound echo signal returned from the object; determining a velocity of the object based on the ultrasound echo signal; displaying a spectral Doppler image showing velocities of the object over time; selecting an interval within a range of the velocities shown in the spectral Doppler image and receiving a user input of adjusting an output volume of an audible sound corresponding to velocities in the selected interval; and outputting, based on the adjusted output volume of the audible sound, an audible sound representing the velocities of the object over time.

ADVANTAGEOUS EFFECTS OF DISCLOSURE

According to some embodiments, it is possible to measure velocities of an object and output detailed information about velocities in an interval selected by the user from among the measured velocities. Furthermore, according to some embodiments, it is possible to selectively adjust an ultrasound Doppler sound signal.

BRIEF DESCRIPTION OF DRAWINGS

FIGS. 7A and 7B illustrate examples in which an ultrasound diagnosis apparatus receives a user input of adjusting a sound volume with respect to a selected velocity interval, according to some embodiments.

BEST MODE

Figure 1:
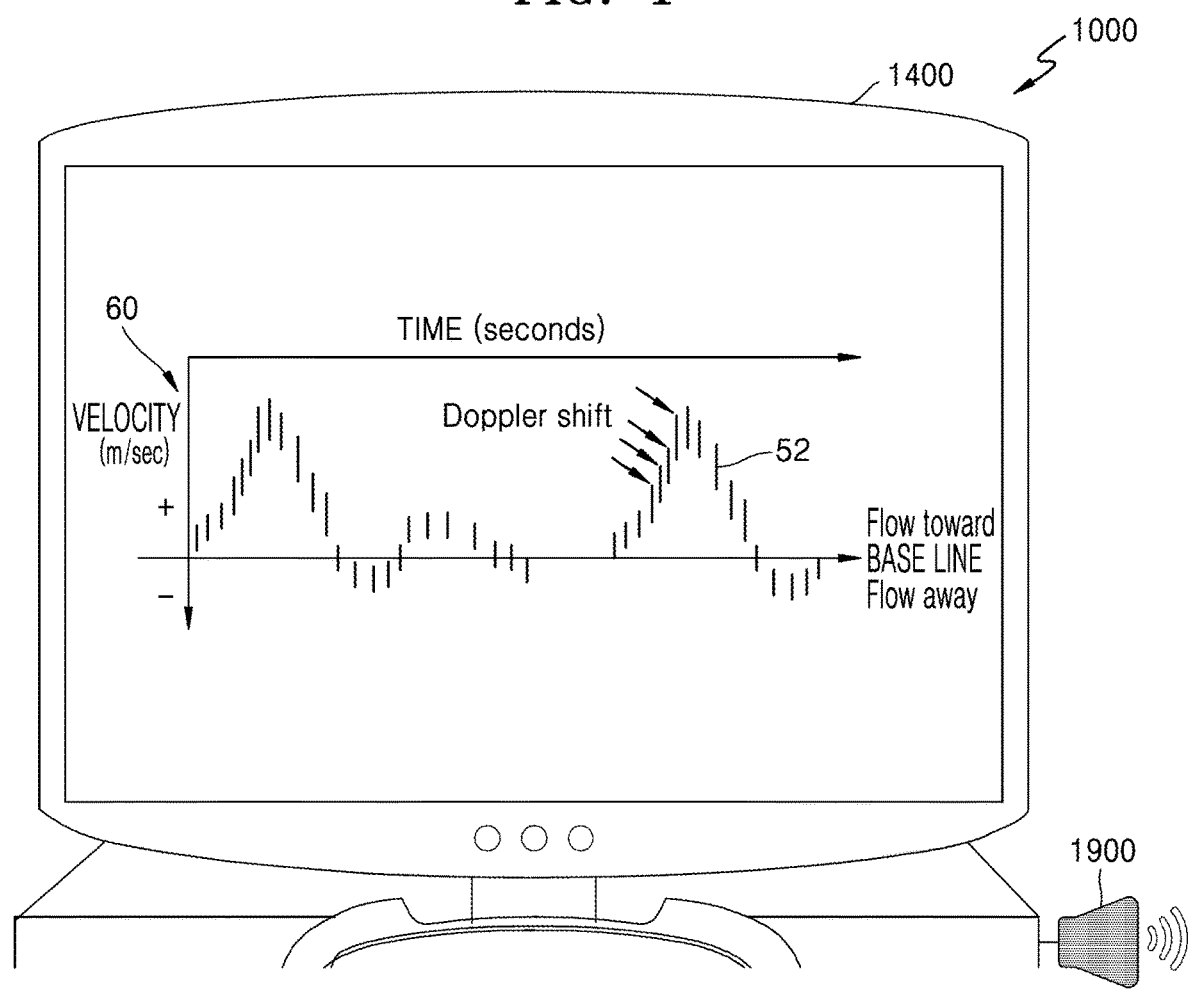
FIG. 1 illustrates an example in which an ultrasound diagnosis apparatus displays velocities of an object, according to some embodiments.

In order to achieve the above-described technical problems, according to a first aspect of the present disclosure, a method of outputting a velocity of an object includes: transmitting an ultrasound signal to an object and receiving an ultrasound echo signal returned from the object; determining a velocity of the object based on the ultrasound echo signal; displaying a spectral Doppler image showing velocities of the object over time; receiving user inputs of selecting an interval within a range of the velocities of the object shown in the spectral Doppler image and adjusting an output volume of an audible sound corresponding to velocities in the selected interval; and outputting, based on the adjusted output volume of the audible sound, an audible sound representing the velocities of the object over time.

Furthermore, the outputting of the audible sound representing the velocities of the object over time based on the adjusted output volume of the audible sound may include adjusting the output volume of the audible sound corresponding to the velocities in the interval within the range of the velocities of the object by adjusting, based on a user input, a power of a Doppler shift frequency corresponding to the interval.

Furthermore, the outputting of the audible sound representing the velocities of the object over time based on the adjusted output volume of the audible sound may include outputting an audible sound representing the velocities of the object over time by mixing the Doppler shift frequency having the adjusted power with Doppler shift frequencies corresponding to remaining intervals other than the interval within the range of the velocities of the object.

Furthermore, the receiving of the user input of selecting the interval within the range of the velocities of the object shown in the spectral Doppler image may include receiving a user input of splitting the range of the velocities of the object shown in the spectral Doppler image into a plurality of velocity intervals and selecting one of the plurality of velocity intervals.

Furthermore, the receiving of the user input of adjusting the output volume of the audible sound corresponding to the velocities in the selected interval may include displaying, when the user input of splitting the range of the velocities of the object shown in the spectral Doppler image into the plurality of velocity intervals are received, an image showing a distribution of velocities of the object.

Furthermore, the receiving of the user input of adjusting the output volume of the audible sound corresponding to the velocities in the selected interval may include changing, when the user input of adjusting the output volume of the audible sound corresponding to the velocities in the selected interval is received, a sound volume with respect to the velocities in the selected interval within the image showing the distribution of the velocities of the object.

Furthermore, the receiving of the user input of adjusting the output volume of the audible sound corresponding to the velocities in the selected interval may include receiving a user input of manipulating a time gain compensation (TGC) button within a control panel included in the ultrasound diagnosis apparatus.

The method may further include outputting, when the user input of selecting the interval within the range of the velocities of the object is received, only an audible sound corresponding to the selected interval among audible sounds representing the velocities of the object over time.

The method may further include displaying, on a brightness (B) mode image of the object, a color Doppler image showing only velocities in the selected interval among the velocities of the object in a color, when the user input of selecting the interval within the range of the velocities of the object is received.

The method may further include receiving user inputs of selecting a time interval within a time range shown in the spectral Doppler image and adjusting an output volume of an audible sound corresponding to a velocity interval within a range of velocities detected during the selected time interval.

According to a second aspect of the present disclosure, an ultrasound diagnosis apparatus includes: an ultrasound probe configured to transmit an ultrasound signal to an object and receive an ultrasound echo signal returned from the object; a controller configured to determine a velocity of the object based on the ultrasound echo signal; a display configured to display a spectral Doppler image showing velocities of the object over time; a user input unit configured to receive user inputs of selecting an interval within a range of the velocities of the object shown in the spectral Doppler image and adjusting an output volume of an audible sound corresponding to velocities in the selected interval; and an audio output unit configured to output, based on the adjusted output volume of the audible sound, an audible sound representing the velocities of the object over time.

MODE OF DISCLOSURE

Terms used in the present disclosure are those general terms currently widely used in the art in consideration of functions regarding the present disclosure, but the terms may vary according to the intention of those of ordinary skill in the art, precedents, or new technology in the art. Also, specified terms may be arbitrarily selected by the applicant, and in this case, the detailed meaning thereof will be described in the detailed description of the disclosure. Thus, the terms used in the disclosure should be understood not as simple names but based on the meaning of the terms and the overall description of the disclosure.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Embodiments of the present disclosure will be described more fully hereinafter with reference to the accompanying drawings so that they may be easily implemented by one of ordinary skill in the art. However, the present disclosure may be implemented in different forms and should not be construed as being limited to the embodiments set forth herein. In addition, parts not related to the present disclosure are omitted to clarify the description of embodiments. Like reference numerals refer to like elements throughout.

Throughout the specification, an "ultrasound image" refers to an image of an object, which is obtained using ultrasound waves. Furthermore, an "object" may be a human, an animal, or a part of a human or animal. For example, the object may include at least one of be an organ such as the liver, the heart, the womb, the brain, a breast, or the abdomen and a blood vessel. Furthermore, the object may be a phantom, and the phantom may mean a material having a density, an effective atomic number, and a volume that are approximately the same as those of a living organism. For example, the phantom may be a spherical phantom having properties similar to a human body.

Furthermore, throughout the specification, a "user" may be, but is not limited to, a medical expert, such as a medical doctor, a nurse, a medical laboratory technologist, a medical imaging expert, or a technician who repairs a medical apparatus.

Embodiments will be described more fully hereinafter with reference to the accompanying drawings FIG. 1 illustrates an example in which an ultrasound diagnosis apparatus 1000 displays velocities of an object, according to some embodiments.

The ultrasound diagnosis apparatus 1000 may calculate a Doppler shift frequency with respect to time based on a difference between frequencies of an ultrasound signal transmitted to an object and an ultrasound echo signal reflected from the object. Furthermore, the ultrasound diagnosis apparatus 1000 may display a graph 60 representing a Doppler shift frequency of the object with respect to time.

A Doppler shift frequency 52 of the object at an arbitrary time point may include a plurality of frequency components. For example, if the object is blood flow within a carotid artery, blood flow through a cross-section of the carotid artery may be a flow of a plurality of blood cells. As flow velocities of the plurality of blood cells are different from one another, the Doppler shift frequency 52 of the blood flow through cross-section of the carotid artery may have a plurality of frequency components. Accordingly, in the graph 60 representing a Doppler shift frequency with respect to time, a Doppler shift frequency at any arbitrary time point may be represented as a straight line having highest and lowest values.

Furthermore, some of the blood cells flowing through a cross-section of a carotid artery at an arbitrary time point may move at the same or similar velocities. In this case, as the number of blood cells moving at the same or similar velocities increases, a power of a Doppler shift frequency corresponding to a velocity of the blood cells may increase. The ultrasound diagnosis apparatus 1000 may display the power of a Doppler shift frequency at an arbitrary time point in a brightness level or color. Thus, in the graph 60 representing a Doppler shift frequency with respect to time, Doppler shift frequencies at arbitrary time points may have different brightness levels.

Since a Doppler shift frequency is located in a frequency range of an audible sound, the ultrasound diagnosis apparatus 1000 may output an audible sound having a range of the Doppler shift frequency via an audio output unit 1900, thereby outputting a measured velocity of the object. A user may determine the presence of an abnormality in the object based on the output audible sound. For example, each object may have a unique pattern of audible sound. Thus, the user may determine the presence of an abnormality in the object based on whether a pattern of the output audible sound is different from a unique pattern generally created by the object. Furthermore, the user may determine the presence of the abnormality in the object based on whether there is an abnormally high- or low-pitched sound in the output audible sound.

Furthermore, the ultrasound diagnosis apparatus 1000 may display the graph 60 representing velocities of the object with respect to time. A Doppler shift frequency is proportional to a velocity of the object, and the ultrasound diagnosis apparatus 1000 may calculate a velocity of the object with respect to time based on a measured Doppler shift frequency.

[Equation 1]

$$f_d = f_r - f_o = (2 \lambda f_o \lambda v \times \cos \theta)/c \quad (1)$$

In Equation (1), $f_o$ is a transmitted frequency, $f_r$ is a received frequency, v is a velocity of an object, c is a speed of sound in a living organism, and $\theta$ is a Doppler angle which may be an angle between a direction in which an ultrasound echo signal reflected from the object is received and a direction in which the object moves. The Doppler angle $\theta$ may be input by the user, or may be determined based on a tilt of a probe or an anatomical structure of the object determined from a brightness (B) mode image of the object. The ultrasound diagnosis apparatus 1000 may use the Doppler angle $\theta$ to convert a Doppler shift frequency $f_d$ into a velocity v of the object, based on the Equation (1).

As described above, some of the blood cells flowing through a cross-section of a carotid artery at an arbitrary time point may move at the same or similar velocities. As more blood cells move at the same or similar velocities, the ultrasound diagnosis apparatus 1000 may display a point representing a velocity more brightly.

Accordingly, the ultrasound diagnosis apparatus 1000 may provide a user with an image produced by visualizing an output audible sound. According to an embodiment, an image representing velocities of the object over time may be referred to as a spectral Doppler image.

Figure 2:
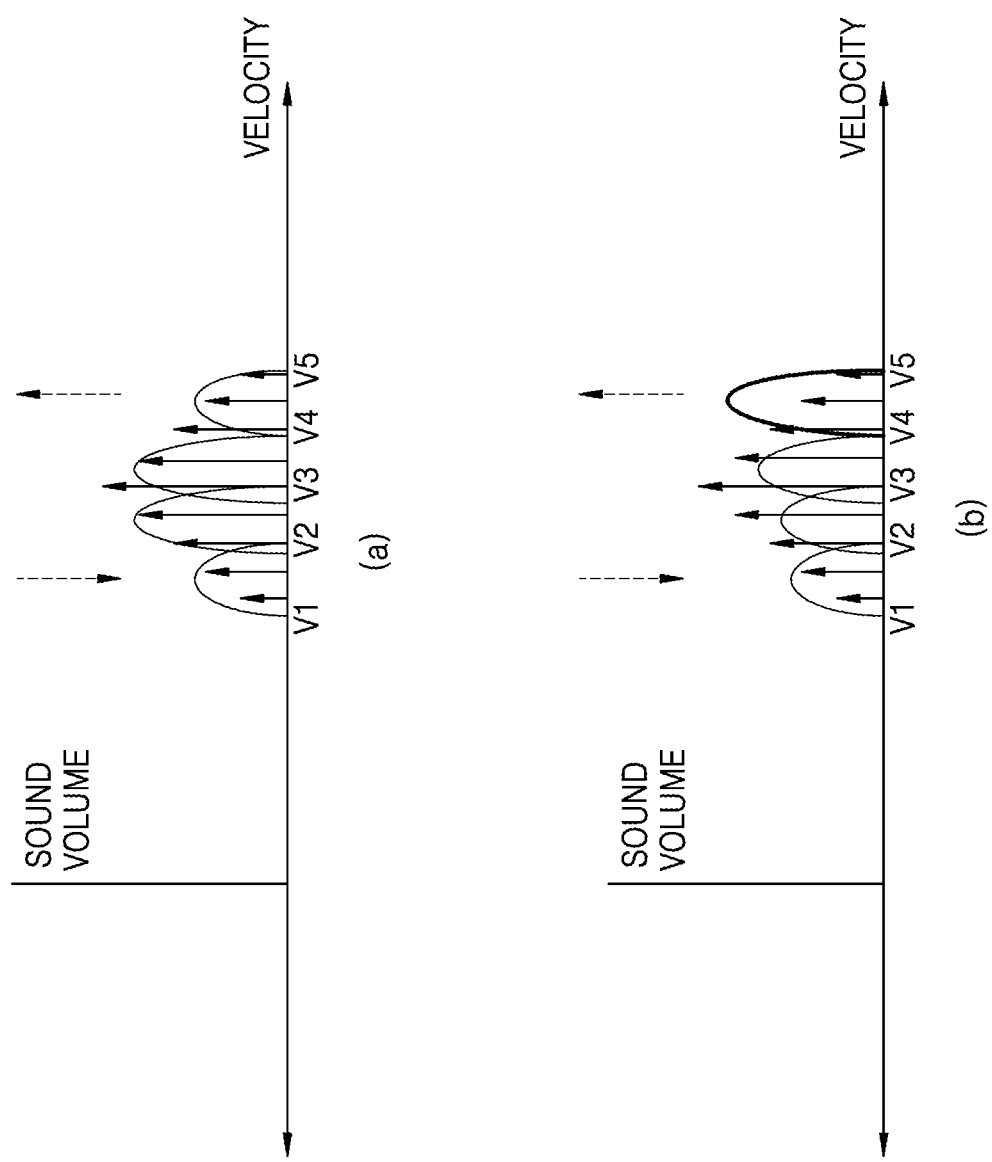
FIG. 2 illustrates an example in which an ultrasound diagnosis apparatus adjusts a volume of an audible sound corresponding to a selected velocity interval, according to some embodiments.

FIG. 2 illustrates an example in which the ultrasound diagnosis apparatus 1000 adjusts a volume of an audible sound corresponding to a selected velocity interval, according to some embodiments.

Referring to FIG. 2, the ultrasound diagnosis apparatus 1000 may provide detailed information about movement of an object by adjusting a volume of an audible sound corresponding to a velocity interval selected by a user.

As shown in FIG. 2A, the ultrasound diagnosis apparatus 1000 may calculate velocities of the object during consecutive time intervals and display an image showing distribution of the calculated velocities of the object.

As shown in FIG. 2B, the ultrasound diagnosis apparatus 1000 may provide a function of selecting an interval within a range of velocities of the object and adjusting a volume of an audible sound corresponding to the selected interval. For example, the ultrasound diagnosis apparatus 1000 may select an interval of V4 to V5 within a range of velocities of the object and receive a user input of increasing a volume of an audible sound corresponding to the selected interval. When the user input of increasing the volume of the audible sound is received, the ultrasound diagnosis apparatus 1000 may output an audible sound of the object with respect to time by mixing the audible sound having the increased volume with an audible sound corresponding to the remaining non-selected velocity intervals. Accordingly, the user may listen to more detailed information about a desired velocity interval among pieces of information about velocities of the object.

Figure 3:
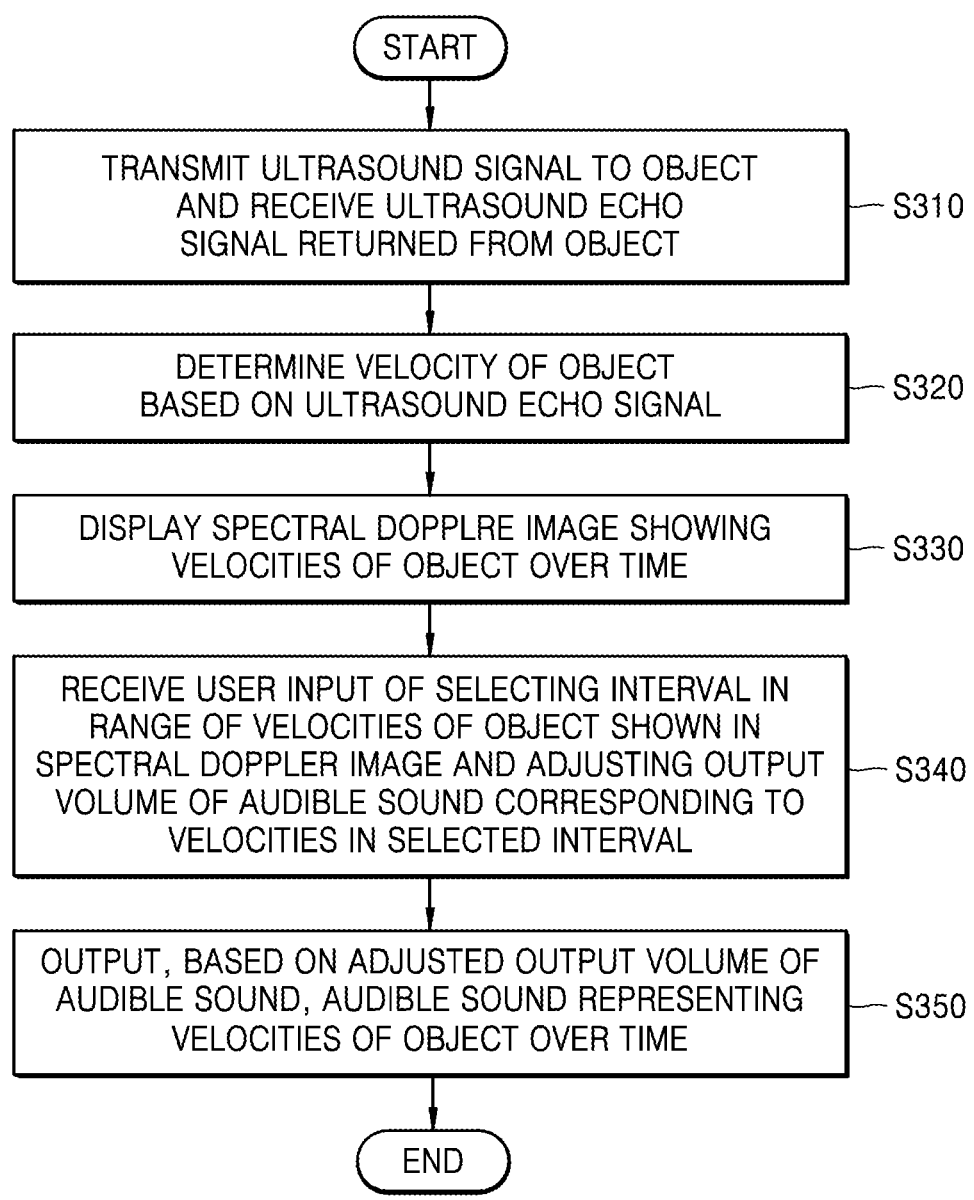
FIG. 3 is a flowchart of a method by which an ultrasound diagnosis apparatus adjusts a volume of an audible sound corresponding to a selected velocity interval, according to some embodiments.

FIG. 3 is a flowchart of a method by which the ultrasound diagnosis apparatus 1000 adjusts a volume of an audible sound corresponding to a selected velocity interval, according to some embodiments.

In step S310, the ultrasound diagnosis apparatus 1000 may transmit an ultrasound signal to an object and receive an ultrasound echo signal returned from the object.

In step S320, the ultrasound diagnosis apparatus 1000 may determine a velocity of the object based on the ultrasound echo signal.

In step S330, the ultrasound diagnosis apparatus 1000 may display a spectral Doppler image showing velocities of the object with respect to time.

In step S340, the ultrasound diagnosis apparatus 1000 may receive user inputs of selecting an interval within a range of the velocities shown in the spectral Doppler image and adjusting an output volume of an audible sound corresponding to velocities in the selected interval.

In step S350, the ultrasound diagnosis apparatus 1000 may output an audible sound representing the velocities of the object with respect to time based on the adjusted output volume of the audible sound.

Figure 4:
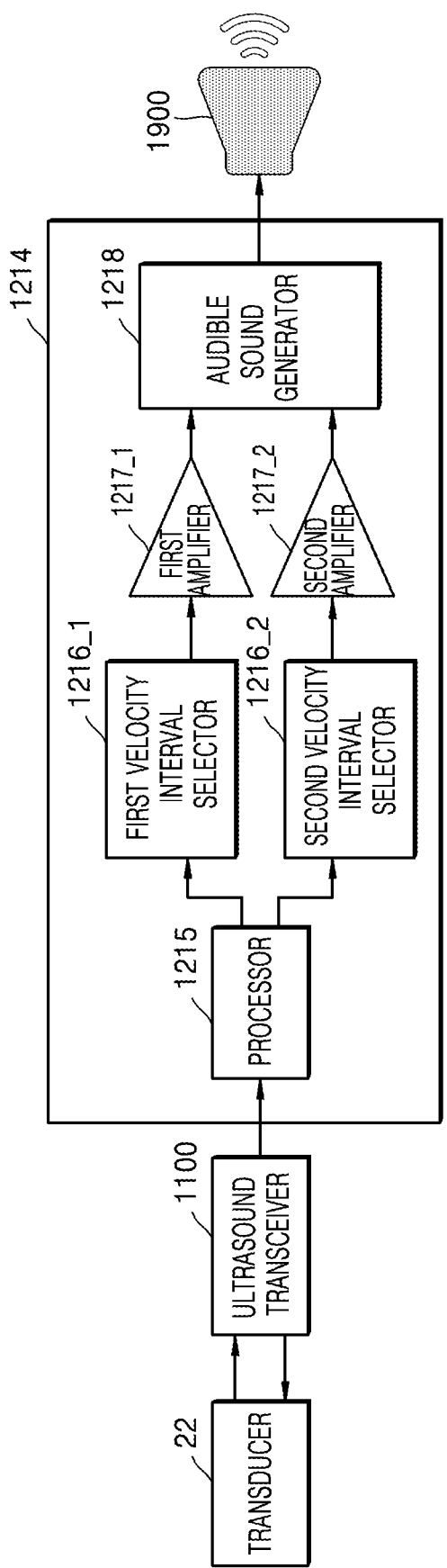
FIG. 4 is a block diagram of an ultrasound diagnosis apparatus for adjusting a volume of an audible sound corresponding to a selected velocity interval, according to some embodiments.

FIG. 4 is a block diagram of an ultrasound diagnosis apparatus 1000 for adjusting a volume of an audible sound corresponding to a selected velocity interval, according to some embodiments.

Referring to FIG. 4, the ultrasound diagnosis apparatus 1000 may include a transducer 22, an ultrasound transceiver 1100, a Doppler processor 1214, and an audio output unit 1900. Furthermore, the Doppler processor 1214 may include a processor 1215, first and second velocity interval selectors 1216_1 and 1216_2, first and second amplifiers 1217_1 and 1217_2, and audible sound generator 1218.

The transducer 22 may be included in a probe (not shown) and transmit an ultrasound signal to an object and receive an echo signal reflected from the object in response to a driving signal applied by the ultrasound transceiver 1100.

The ultrasound transceiver 1100 may drive the probe so that the transducer 22 may generate a pulse wave with a pulse repetition frequency (PRF) and a continuous wave. Furthermore, the ultrasound transceiver 1100 may receive the ultrasound echo signal from the transducer 22 to thereby convert the received ultrasound echo signal into digital data.

The Doppler processor 1214 may receive digital data into which the ultrasound echo signal has been converted from the ultrasound transceiver 1100. The Doppler processor 1214 may be an arithmetic unit for analyzing or extracting a Doppler shift frequency based on the ultrasound echo signal. For example, the processor 1215 may calculate a Doppler shift frequency of the object with respect to time by performing Fourier Transform or Fast Fourier Transform on the digital data into which the ultrasound echo signal has been converted.

The ultrasound diagnosis apparatus 1000 may receive a user input of selecting an interval within a range of Doppler shift frequency from the user. Furthermore, the ultrasound diagnosis apparatus 1000 may receive a user input of selecting a velocity interval in a range of velocities of the object from the user. In this case, the ultrasound diagnosis apparatus 1000 may determine an interval of Doppler shift frequency corresponding to the selected velocity interval.

The processor 1215 may control the first and second velocity interval selectors 1216_1 and 1216_2 such that the range of Doppler shift frequency is divided into an interval selected by the user and an interval not selected by the user. For example, the processor 1215 may control the first and second velocity interval selectors 1216_1 and 1216_2 such that the first velocity interval selector 1216_1 selects the interval selected by the user in the range of Doppler shift frequency and the second velocity interval selector 1216_2 selects the interval not selected by the user.

Furthermore, the processor 1215 may control the first amplifier 1217_1 such that an audible sound having a frequency corresponding to the interval selected by the user in the range of Doppler shift frequency of the object is output with a sound volume adjusted by the user and control the second amplifier 1217_2 such that an audible sound having a frequency corresponding to the interval not selected by the user is output with a preset volume.

The audible sound generator 1218 may generate an audio signal representing a Doppler shift frequency of the object by mixing a frequency amplified by the first amplifier 1217_1 with a frequency amplified by the second amplifier 1217_2. The generated audio signal may be output via the audio output unit 1900 as an audible sound.

Figure 5:
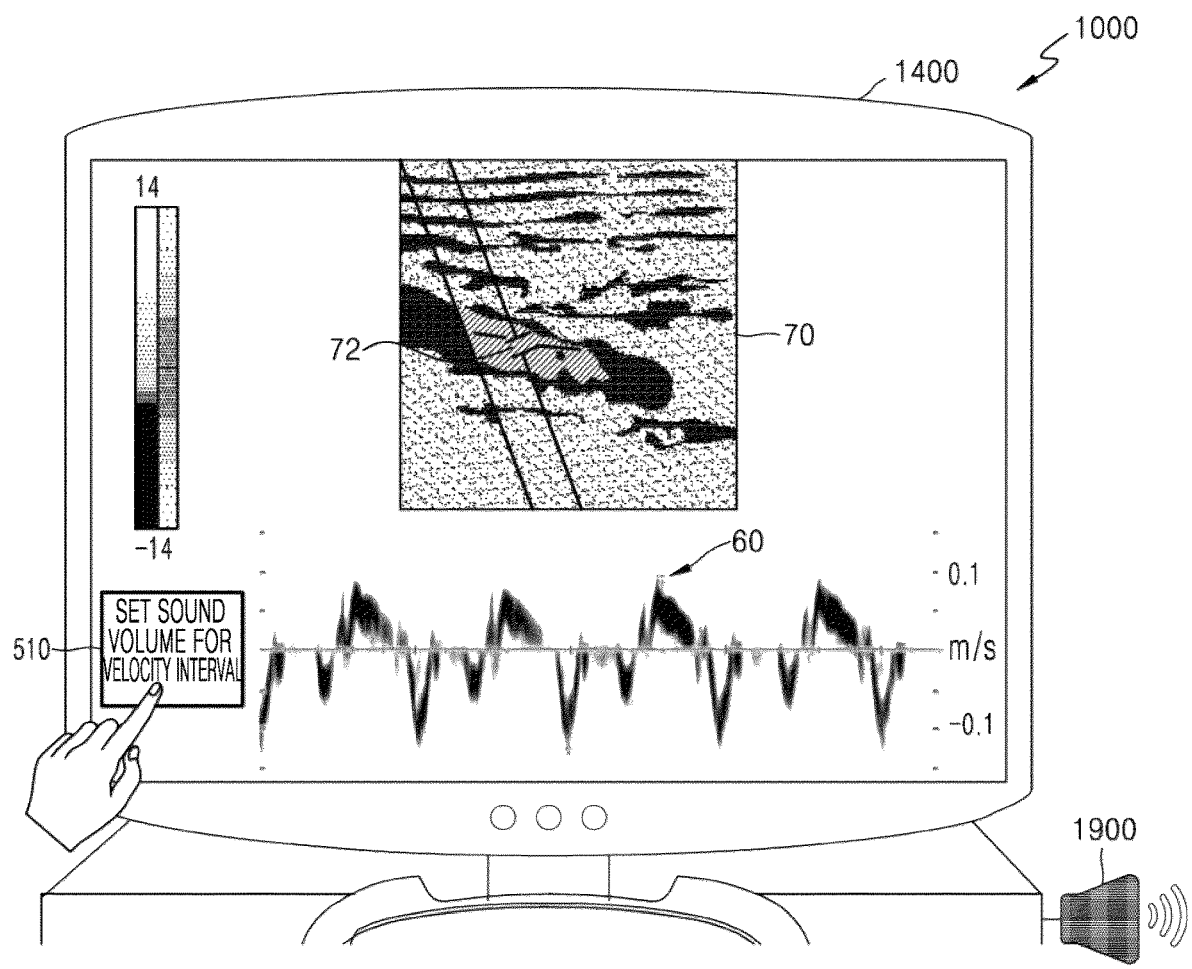
FIG. 5 illustrates an example in which an ultrasound diagnosis apparatus displays velocities of an object, according to some embodiments.

FIG. 5 illustrates an example in which an ultrasound diagnosis apparatus 1000 displays velocities of an object, according to some embodiments.

Referring to FIG. 5, the ultrasound diagnosis apparatus 1000 may display velocities of an object as a color Doppler image 70 and a spectral Doppler image 60.

The ultrasound diagnosis apparatus 1000 may transmit an ultrasound signal to the object and receive an ultrasound echo signal reflected from the object according to a user input. If the object is a carotid artery in a patient, as shown in FIG. 5, the ultrasound diagnosis apparatus 1000 may display the color Doppler image and the spectral Doppler image 60, both representing velocities of blood flow through the carotid artery.

The ultrasound diagnosis apparatus 1000 may display, on a B mode image showing the carotid artery in a patient, the color Doppler image 70 representing a direction of blood flow through a carotid artery in a certain color and velocities of the blood flow as an arrow or saturation level.

Furthermore, the ultrasound diagnosis apparatus 1000 may receive a user input of setting a sample gate 72 on the carotid artery in the color Doppler image 70. According to an embodiment, the ultrasound diagnosis apparatus 1000 may receive a user input of setting the sample gate 72 in the B mode image but not in the color Doppler image 70.

The ultrasound diagnosis apparatus 1000 may display the spectral Doppler image 60 showing velocities of blood flow in a region on which the sample gate 72 is set with respect to time. In this case, the blood flow through the region where the sample gate 72 is set at an arbitrary time point may have a range of velocities rather than a single velocity. Accordingly, as shown in the spectral Doppler image 60 of FIG. 5, a velocity of blood flow through the region where the sample gate 72 is set at an arbitrary time point may be displayed as a range of velocities having lowest and highest values.

Furthermore, the ultrasound diagnosis apparatus 1000 may output via the audio output unit 1900 an audible sound representing velocities of blood flow through the region where the sample gate 72 is set. Since the blood flow through the region at an arbitrary time point may have a range of velocities rather than a single velocity, an audible sound output at the arbitrary time point may have a range from lowest to highest frequencies.

Furthermore, the ultrasound diagnosis apparatus 1000 may provide a user interface for adjusting a volume of an audible sound corresponding to a velocity interval selected by the user. For example, the ultrasound diagnosis apparatus 1000 may display, together with the spectral Doppler image 60, a button 510 for adjusting a volume of an audible sound corresponding to a velocity interval selected by the user. Furthermore, the ultrasound diagnosis apparatus 1000 may receive a user input of selecting a preset button within a control panel.

Figure 6A:
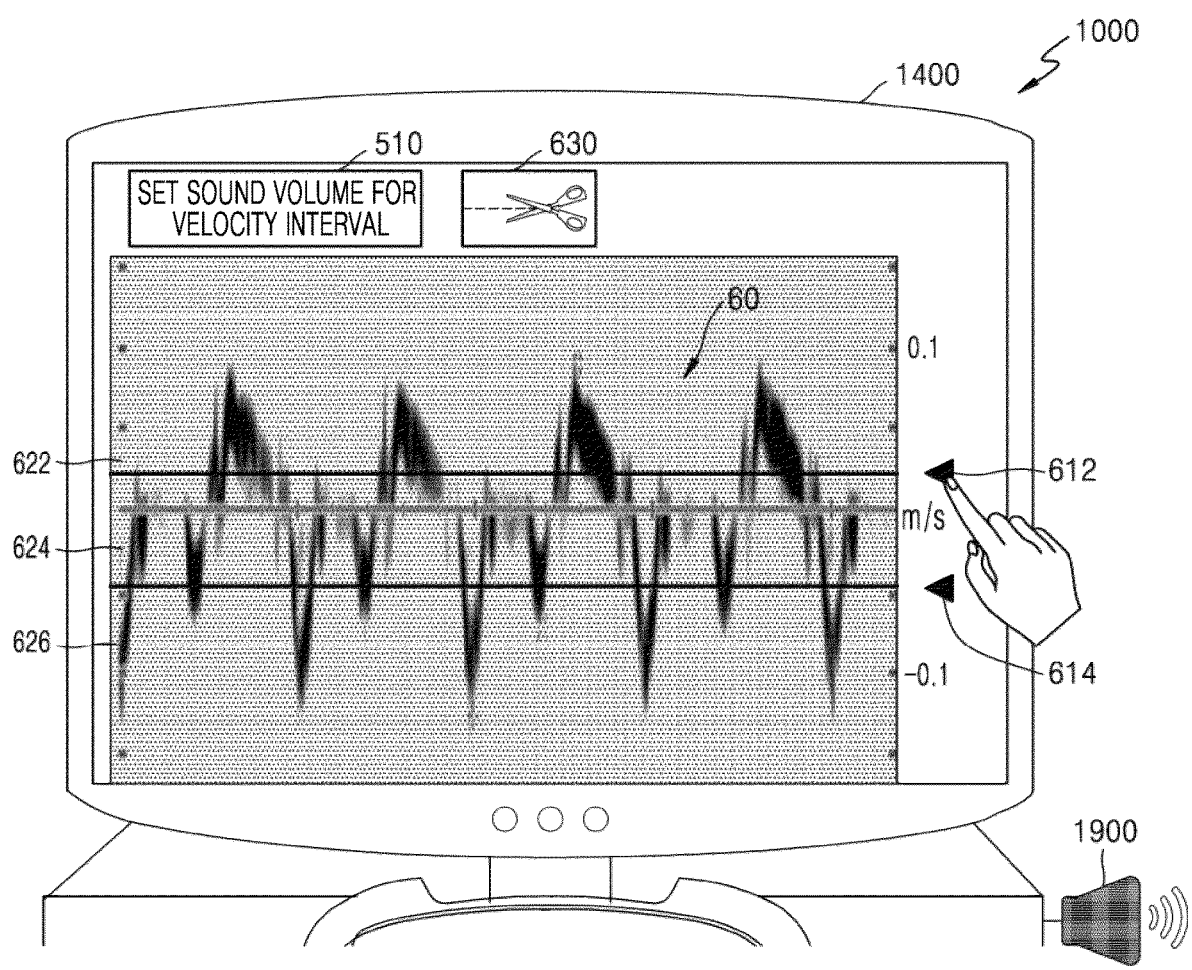
FIG. 6A illustrates an example in which an ultrasound diagnosis apparatus receives a user input of setting a velocity interval, according to some embodiments.

FIG. 6A illustrates an example in which an ultrasound diagnosis apparatus 1000 receives a user input of setting a velocity interval, according to some embodiments.

Referring to FIG. 6A, the ultrasound diagnosis apparatus 1000 may provide a user interface for setting a velocity interval.

For example, the ultrasound diagnosis apparatus 1000 may display a button 630 for splitting a range of velocities of an object. When a user input of selecting the button 630 is received, the ultrasound diagnosis apparatus 1000 may display first and second indicators 612 and 614 for splitting a range of velocities on a velocity axis representing a velocity. After selecting the first and second indicators 612 and 614 and then receiving a user input of moving the selected first and second indicators 612 and 614, the ultrasound diagnosis apparatus 1000 may split a range of velocities displayed in a spectral Doppler image 60 based on velocities indicated by the moved first and second indicators 612 and 614. Furthermore, the ultrasound diagnosis apparatus 1000 may display, on the spectral Doppler image 60, images 622, 624, and 626 respectively indicating velocity intervals into which the range of velocities are split.

For example, after receiving a user input of positioning the first and second indicators 612 and 614 on the velocity axis such that the first and second indicators 612 and 614 respectively indicate 0.02 m/s and −0.05 m/s, the ultrasound diagnosis apparatus 1000 may split a velocity range of −0.1 m/s to 0.1 m/s into intervals of −0.1 m/s to −0.05 m/s, −0.05 m/s to 0.02 m/s, and 0.02 m/s to 0.1 m/s.

Furthermore, when a user input of moving the selected first and second indicators 612 and 614 is received, the ultrasound diagnosis apparatus 1000 may output an audible sound corresponding to velocities indicated by the first and second indicators 612 and 614.

Figure 6B:
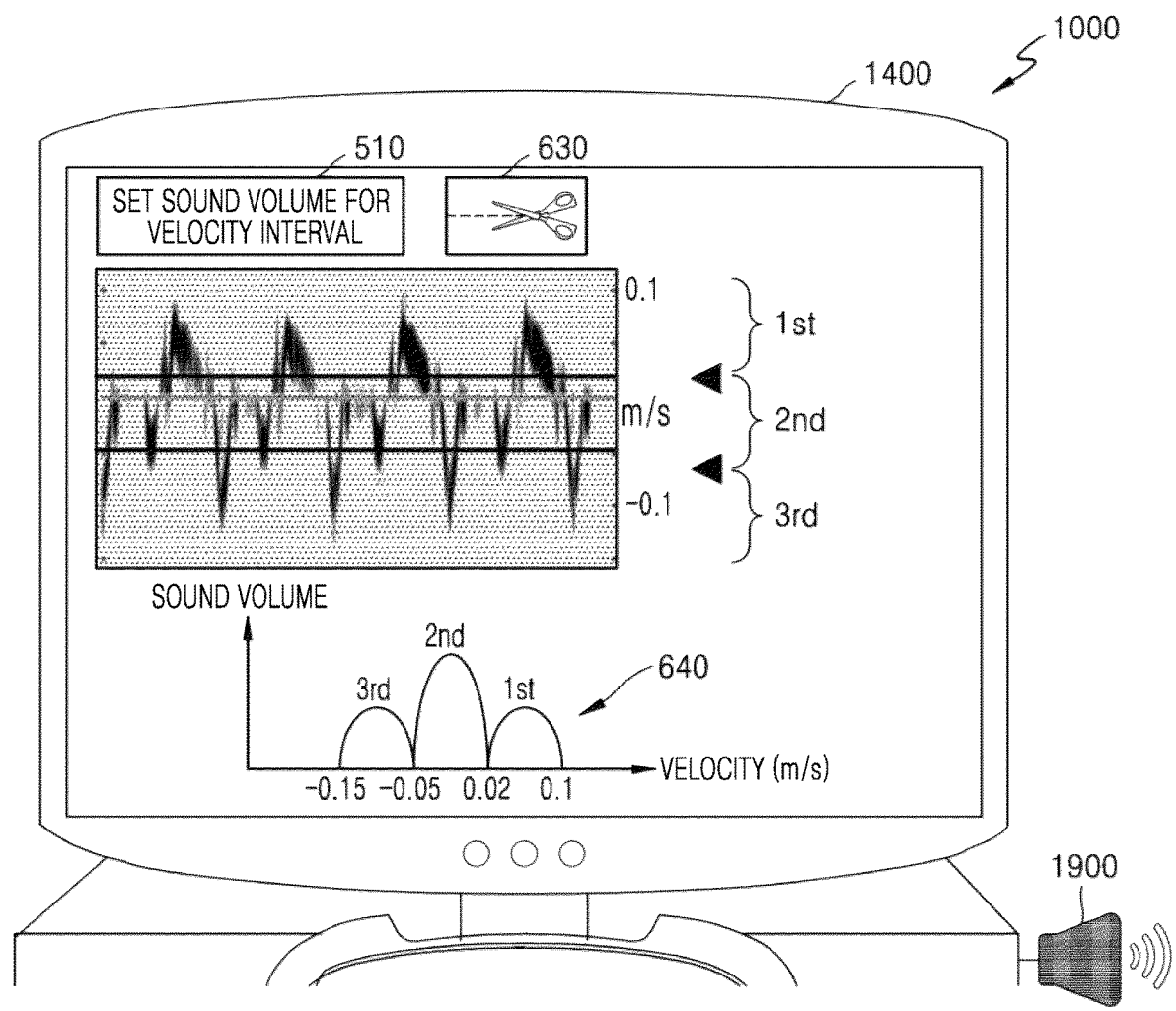
FIG. 6B illustrates an example in which an ultrasound diagnosis apparatus displays distribution of a plurality of velocity intervals into which a range of velocities of an object are split, according to some embodiments.

FIG. 6B illustrates an example in which an ultrasound diagnosis apparatus 1000 displays distribution of a plurality of velocity intervals into which a range of velocities of an object are split, according to some embodiments.

Referring to FIG. 6B, as a range of velocities of an object are split into a plurality of velocity intervals, the ultrasound diagnosis apparatus 1000 may display an image 640 representing a distribution of the plurality of velocity intervals.

For example, a sound volume with respect to a first velocity interval may be proportional to the number of times that velocities in the first velocity interval are detected during a time range over which velocities of the object are displayed. Furthermore, the sound volume with respect to the first velocity interval may be proportional to a length of time during which the velocities in the first velocity interval are detected during the time range over which the velocities of the object are displayed. Furthermore, the sound volume with respect to the first velocity interval may be proportional to a power of Doppler shift frequency components corresponding to the velocities in the first velocity interval during the time range over which the velocities of the object are displayed. Furthermore, the sound volume with respect to the first velocity interval may be proportional to a power of audible sound corresponding to the velocities in the first velocity interval during the time range over which the velocities of the object are displayed.

Figure 7B:
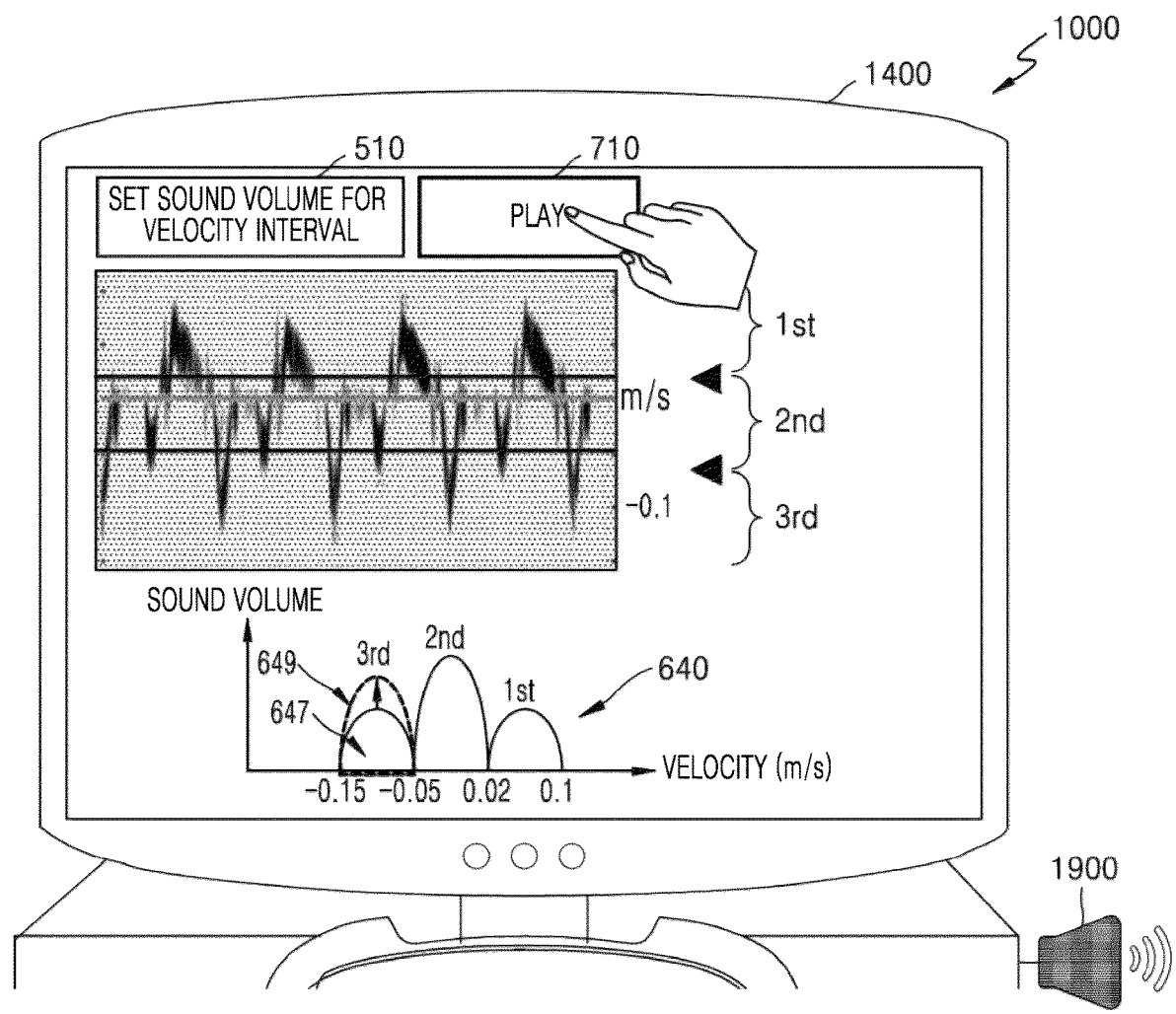

FIGS. 7A and 7B illustrate examples in which an ultrasound diagnosis apparatus 1000 receives a user input of adjusting a sound volume with respect to a selected velocity interval, according to some embodiments.

Referring to FIG. 7A, the ultrasound diagnosis apparatus 1000 may receive a user input of selecting one of a plurality of velocity intervals.

When the user input of selecting one of the plurality of velocity intervals is received, the ultrasound diagnosis apparatus 1000 may display, on an image 640 showing a distribution of the plurality of velocity intervals, an indicator 645 indicating that a sound volume with respect to the selected velocity interval can be adjusted. For example, if a user input of selecting a third velocity interval among the plurality of velocity intervals is received, the ultrasound diagnosis apparatus 1000 may display, on the image 640 showing a distribution of the plurality of velocity intervals, the indicator 645 indicating that a sound volume with respect to the third velocity interval can be adjusted.

Furthermore, when a user input of selecting at least one of the plurality of velocity intervals is received, the ultrasound diagnosis apparatus 1000 may output only an audible sound corresponding to the selected at least one velocity interval among the entire range of audible sound that can be output over time. Thus, the user may identify whether a desired velocity interval with respect to which a sound volume is to be adjusted has been correctly selected.

Furthermore, the ultrasound diagnosis apparatus 1000 may receive a user input of adjusting a sound volume with respect to a selected velocity interval. For example, the ultrasound diagnosis apparatus 1000 may display a user interface 702 for adjusting a sound volume with respect to a selected velocity interval and receive a user input of adjusting the sound volume with respect to the selected velocity interval via the displayed user interface 702.

As another example, the ultrasound diagnosis apparatus 1000 may adjust a sound volume with respect to a selected velocity interval, based on a user input for buttons within a control panel included in the ultrasound diagnosis apparatus 1000.

For example, time gain compensation (TGC) buttons 704 within the control panel may respectively correspond to the plurality of velocity intervals. For example, the ultrasound diagnosis apparatus 1000 may determine the sound volume with respect to the third velocity interval, based on a user input of moving a position of a third TGC button.

As another example, a plurality of circular dials in the control panel may respectively correspond to the plurality of velocity intervals. When a user input of turning one of the plurality of circular dials is received, the ultrasound diagnosis apparatus 1000 may change a sound volume with respect to a velocity interval corresponding to the turned circular dial among the plurality of velocity intervals.

Buttons used to adjust a sound volume with respect to a selected velocity interval are not limited to TGC buttons or a plurality of circular dials, and various types of buttons may be used according to user's settings.

Referring to FIG. 7B, the ultrasound diagnosis apparatus 1000 may display an adjusted sound volume with respect to a velocity interval. For example, the ultrasound diagnosis apparatus 1000 may display a sound volume 647 with respect to a third velocity interval, which has not been adjusted, together with an adjusted sound volume 649 with respect to the third velocity interval, thereby allowing a comparison between the sound volumes 647 and 649 with respect to the third velocity interval before and after being adjusted.

Furthermore, when a user input of adjusting a sound volume with respect to at least one of a plurality of velocity intervals is received, the ultrasound diagnosis apparatus 1000 may adjust a power of audible sound corresponding to a velocity interval with respect to which a sound volume has been adjusted. For example, the ultrasound diagnosis apparatus 1000 may adjust, based on the adjusted sound volume with respect to the velocity interval, a power of Doppler shift frequency corresponding to the velocity interval with respect to which the sound volume has been adjusted, thereby adjusting a power of audible sound corresponding to the velocity interval.

The ultrasound diagnosis apparatus 1000 may output, based on the adjusted power of audible sound, an audible sound representing the entire velocity of an object with respect to time. The ultrasound diagnosis apparatus 1000 may display a button 710 for outputting again the audible sound representing the entire velocity of the object with respect to time. When a user input of selecting the button 710 is received, the ultrasound diagnosis apparatus 1000 may output the audible sound representing the entire velocity of the object with respect to time, based on the adjusted power of the audible sound.

Furthermore, after adjusting the sound volume with respect to the selected velocity interval and then receiving a user input of measuring a velocity of the object, the ultrasound diagnosis apparatus 1000 may output an audible sound representing the measured velocity of the object based on a power of audible sound set with respect to the selected velocity interval. For example, after setting the sound volume with respect to the selected velocity interval to be increased by twice and then receiving a user input of measuring a velocity of the object, the ultrasound diagnosis apparatus 1000 may output an audible sound representing the entire velocity of the object by doubling the power of an audible sound corresponding to the selected velocity interval.

Figure 8:
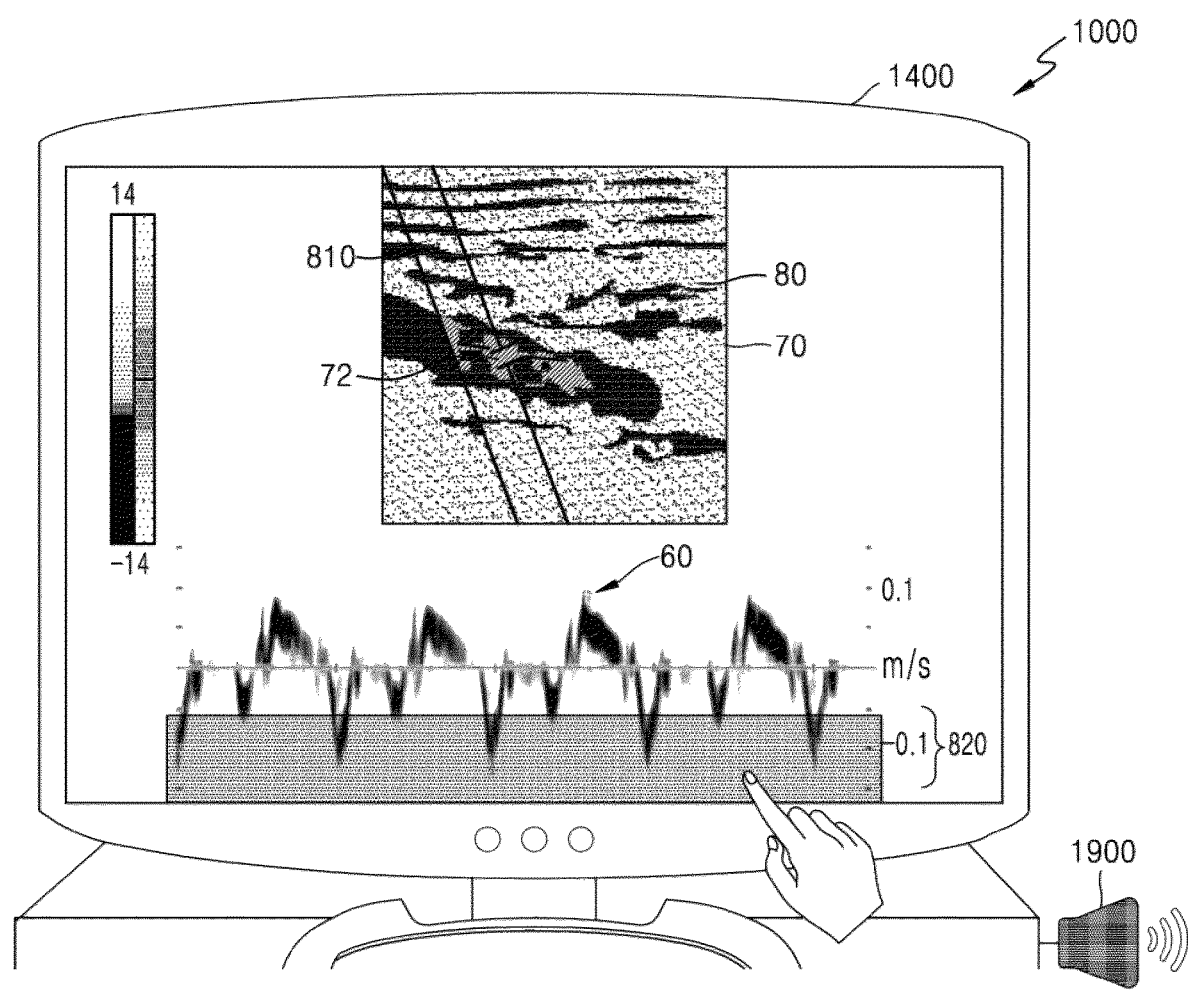
FIG. 8 illustrates an example in which an ultrasound diagnosis apparatus displays a color Doppler image representing a region corresponding to a velocity interval selected by a user, according to some embodiments.

FIG. 8 illustrates an example in which an ultrasound diagnosis apparatus 1000 displays a color Doppler image showing a region corresponding to a velocity interval selected by a user, according to some embodiments.

Referring to FIG. 8, when a user input of selecting a velocity interval within a range of velocities of an object is received, the ultrasound diagnosis apparatus 1000 may display a color Doppler image showing only a part of a region of interest corresponding to the selected velocity interval.

For example, the ultrasound diagnosis apparatus 1000 may set a region of interest 810 in a B mode image 80 based on a user input and display a color Doppler image 70 showing the set region of interest 810. Furthermore, the ultrasound diagnosis apparatus 1000 may set a sample gate 72 in the B mode image 80 and display a spectral Doppler image 60 showing velocities of a region on which the sample gate 72 is set with respect to time.

When a user input of selecting a velocity interval 820 within a range of velocities of the object shown in the spectral Doppler image 60 is received, the ultrasound diagnosis apparatus 1000 may display the color Doppler image 70 showing only a part of the region of interest 810 corresponding to the velocity interval 820 selected by the user. For example, if a user input of selecting a velocity interval of −0.15 m/s to 0.05 m/s is received, the ultrasound diagnosis apparatus 1000 may display only a region where blood flow having velocities of −0.15 m/s to 0.5 m/s is detected from among regions where velocities of blood flow are displayed in such a manner that the region is distinguished from the remaining regions.

In this case, the ultrasound diagnosis apparatus 1000 may play back again only a region corresponding to the selected velocity interval in a previously captured color Doppler moving image, such that the region is distinguished from the remaining regions. Furthermore, the ultrasound diagnosis apparatus 1000 may display only a region corresponding to the selected velocity interval in a newly captured color Doppler image, such that the region is distinguished from the remaining regions.

Figure 9:
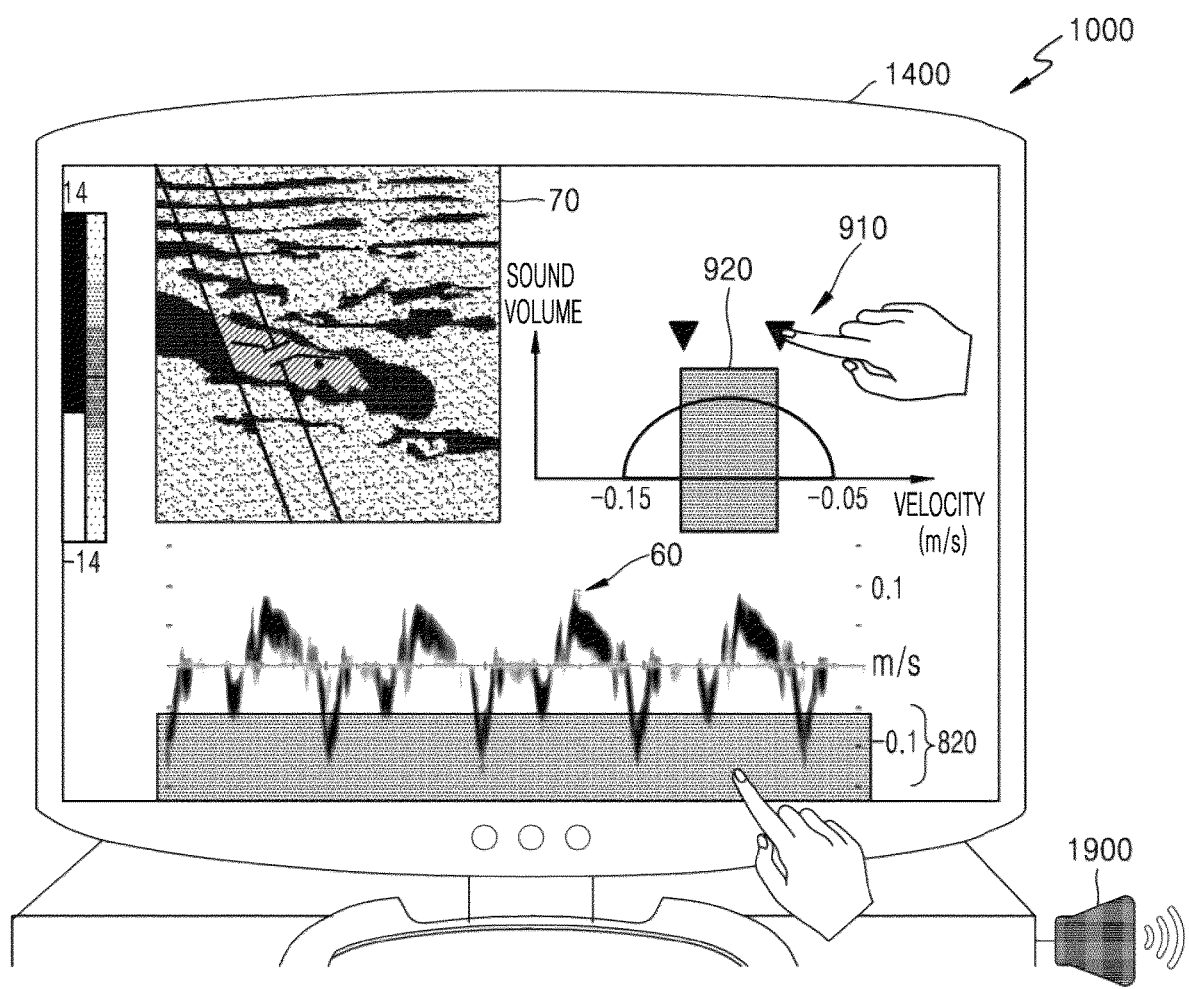
FIG. 9 illustrates an example in which an ultrasound diagnosis apparatus adjusts a sound volume with respect to a sub velocity interval in a velocity interval selected by a user, according to some embodiments.

FIG. 9 illustrates an example in which an ultrasound diagnosis apparatus 1000 adjusts a sound volume with respect to a sub velocity interval in a velocity interval selected by a user, according to some embodiments.

Referring to FIG. 9, the ultrasound diagnosis apparatus 1000 may receive a user input of selecting a sub velocity interval in a velocity interval selected by the user and then a user input of adjusting a sound volume with respect to the selected sub velocity interval.

When a user input of selecting a velocity interval 820 within a range of velocities of an object displayed in the spectral Doppler image 60 is received, the ultrasound diagnosis apparatus 1000 may display an image 910 showing a distribution of velocities in the selected velocity interval 820.

Furthermore, the ultrasound diagnosis apparatus 1000 may receive a user input of further selecting a sub velocity interval 920 in the image 910 showing the distribution of the velocities in the selected velocity interval 820. Furthermore, the ultrasound diagnosis apparatus 1000 may receive a user input of adjusting a sound volume with respect to the selected sub velocity interval 920 and output an audible sound representing the entire velocity of the object over time based on the adjusted sound volume.

Figure 10:
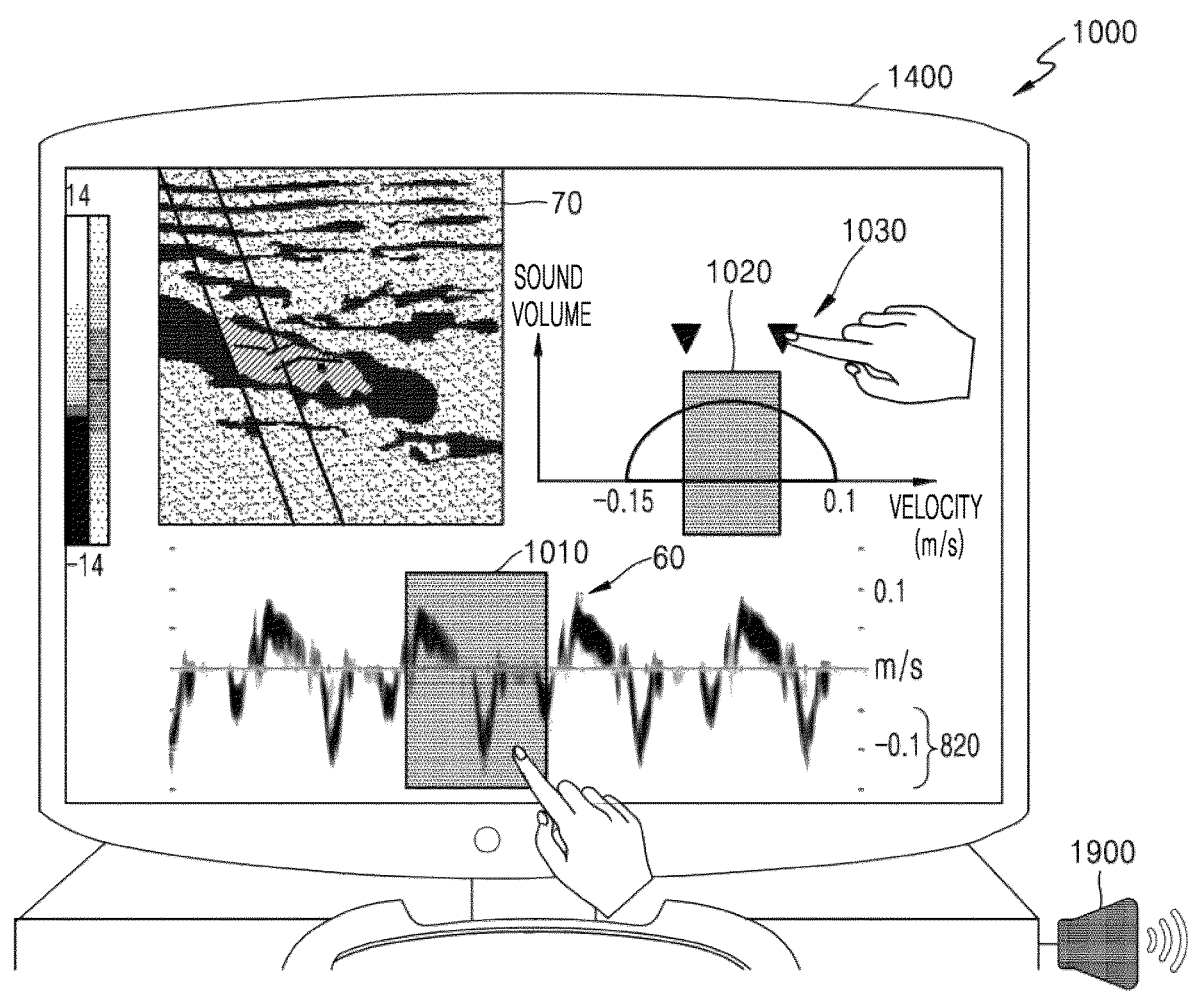
FIG. 10 illustrates an example in which an ultrasound diagnosis apparatus adjusts a sound volume with respect to a velocity interval within a range of velocities during a time interval selected by a user, according to some embodiments.

FIG. 10 illustrates an example in which an ultrasound diagnosis apparatus 1000 adjusts a sound volume with respect to a velocity interval within a range of velocities during a time interval selected by a user, according to some embodiments.

Referring to FIG. 10, the ultrasound diagnosis apparatus 1000 may receive a user input of selecting a time interval 1010 within a time range on a spectral Doppler image 60 and then a user input of adjusting a sound volume with respect to a velocity interval 1020 within a range of velocities during the selected time interval 1010.

When a user input of selecting the time interval 1010 in the time range displayed on the spectral Doppler image 60 of the object is received, the ultrasound diagnosis apparatus 1000 may display an image 1030 showing a distribution of velocities detected during the selected time interval 1010.

Furthermore, the ultrasound diagnosis apparatus 1000 may receive a user input of selecting a velocity interval 1020 in the image 1030 showing the distribution of velocities. Furthermore, the ultrasound diagnosis apparatus 1000 may receive a user input of adjusting a sound volume with respect to the selected velocity interval 1020 and then output, based on the adjusted sound volume, an audible sound representing velocities of the object during the selected time interval 1010.

Figure 11:
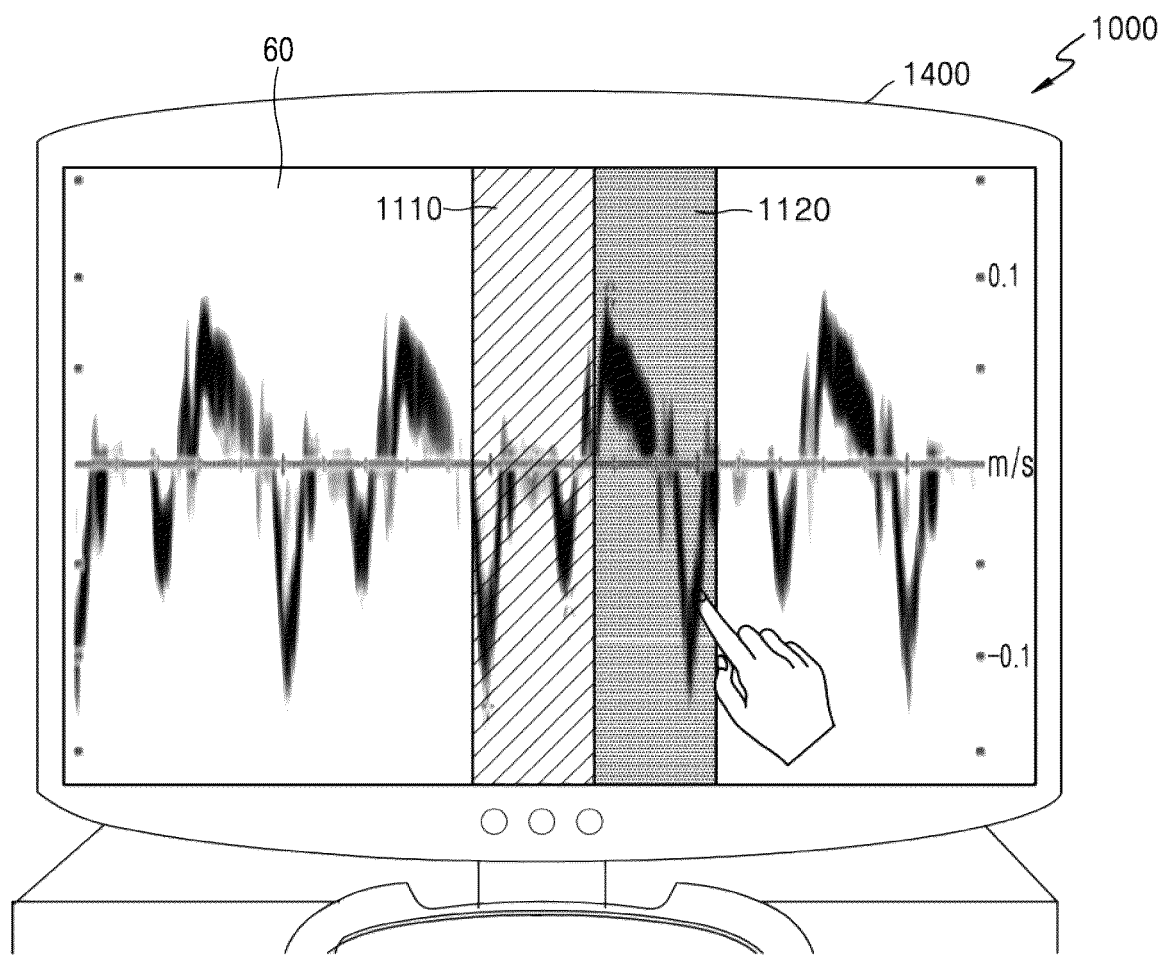
FIG. 11 illustrates an example in which an ultrasound diagnosis apparatus adjusts a volume of an audible sound during a time interval selected by a user, according to some embodiments.

FIG. 11 illustrates an example in which an ultrasound diagnosis apparatus 1000 adjusts a volume of an audible sound during a time interval selected by a user, according to some embodiments.

Referring to FIG. 11, the ultrasound diagnosis apparatus 1000 may receive a user input of selecting a time interval on a spectral Doppler image 60 and adjusting a sound volume of audible sound corresponding to the selected time interval.

For example, the ultrasound diagnosis apparatus 1000 may receive a user input of setting a first audible sound volume with respect to a first time interval 1110 and a second audible sound volume with respect to a second time interval 1120. After receiving a user input of setting a sound volume of audible sound with respect to a time interval and then a user input of outputting an audible sound representing a velocity of an object, the ultrasound diagnosis apparatus 1000 may output an audible sound with the first audible sound volume during the first time interval 1110 and an audible sound with the second audible sound volume during the second time interval 1120.

Figure 12:
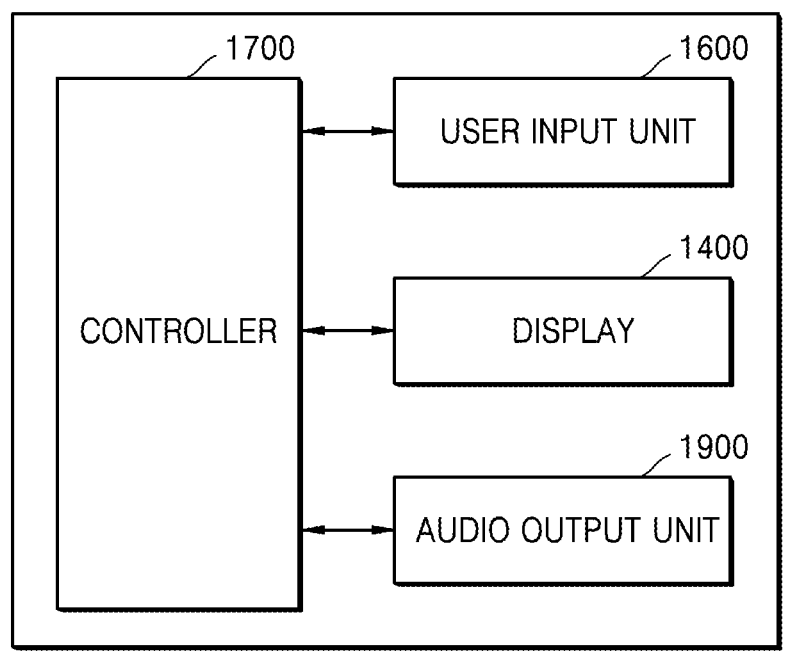
FIG. 12 is a block diagram of a configuration of an ultrasound diagnosis apparatus according to some embodiments.

FIG. 12 is a block diagram of a configuration of an ultrasound diagnosis apparatus 1000 according to some embodiments.

Referring to FIG. 12, the ultrasound diagnosis apparatus 1000 may include a controller 1700, a user input unit 1600, a display 1400, and an audio output unit 1900.

However, all of the components shown in FIG. 12 are not essential components. The ultrasound diagnosis apparatus 100 may be implemented using more or fewer components than those shown in FIG. 12.

While FIG. 12 shows that the user input unit 1600 and the display 1400 are separate components, the user input unit 1600 and the display 1400 may be implemented as a single component such as a touch screen.

The controller 1700 may control all components of the ultrasound diagnosis apparatus 1000.

For example, the controller 1700 may determine a velocity of an object based on an ultrasound echo signal received from the object.

The controller 1700 may also adjust, based on a user input, a power of Doppler shift frequency corresponding to an interval within a range of velocities of the object to thereby adjust an output volume of an audible sound corresponding to velocities in the interval.

The display 1400 may display an ultrasound image and a user interface. For example, the display 1400 may display a spectral Doppler image showing velocities of the object over time.

The user input unit 1600 may receive a user input for controlling the ultrasound diagnosis apparatus 1000. For example, the user input unit 1600 may receive a user input of selecting an interval within a range of velocities of the object shown in the spectral Doppler image and adjusting an output volume of an audible sound corresponding to velocities in the selected interval.

The audio output unit 1900 may output an audio signal generated by the ultrasound diagnosis apparatus 1000. The audio output unit 1900 may output an audible sound representing velocities of the object over time.

Furthermore, the controller 1700 may control the audio output unit 1900 to output an audible sound representing velocities of the object over time by mixing a Doppler shift frequency having an adjusted power with Doppler shift frequencies corresponding to the remaining intervals other than the interval within the range of velocities of the object.

Furthermore, the user input unit 1600 may receive a user input of selecting an interval within a range of velocities of the object by dividing the range of velocities of the object shown in the spectral Doppler image into a plurality of velocity intervals and selecting one of the plurality of velocity intervals.

Furthermore, when a user input of dividing a range of velocities of the object shown in a spectral Doppler image into a plurality of velocity intervals is received, the controller 1700 may control the display 1400 to display an image showing a distribution of the velocities of the object.

Furthermore, when a user input of adjusting an output volume of an audible sound corresponding to velocities in the selected interval is received, the controller 1700 may control the display 1400 to display an adjusted sound volume with respect to an interval selected in the image showing the distribution of the velocities of the object.

Furthermore, the user input unit 1600 may receive a user input of adjusting an output volume of an audible sound corresponding to velocities in a selected interval by receiving a user input of manipulating a TGC button in a control panel provided on the ultrasound diagnosis apparatus 1000.

Furthermore, when a user input of selecting an interval within a range of velocities of the object is received, the controller 1700 may control the audio output unit 1900 to output only an audible sound corresponding to the selected interval among audible sounds representing the velocities of the object over time.

Furthermore, when a user input of selecting an interval within a range of velocities of the object is received, the controller 1700 may control the display 1400 to display, on a B mode image of the object, a color Doppler image showing only velocities in the selected interval among the velocities of the object in a color.

Furthermore, the user input unit 1600 may receive a user input of selecting a time interval within a time range shown in a spectral Doppler image and adjusting an output volume of an audible sound corresponding to a velocity interval within a range of velocities detected during the selected time interval.

Figure 13:
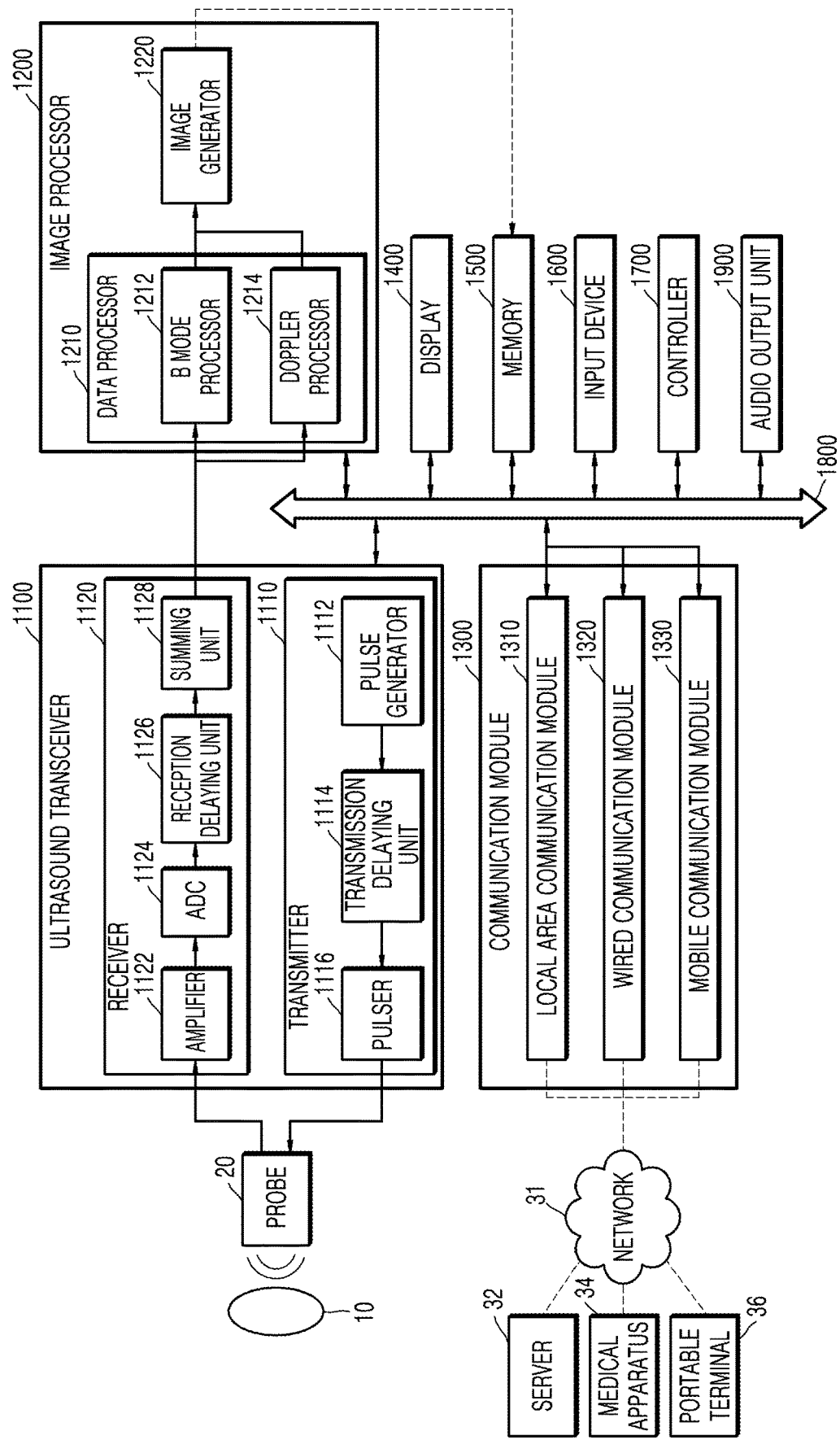
FIG. 13 is a block diagram of a configuration of an ultrasound diagnosis apparatus according to other embodiments.

FIG. 13 is a block diagram of a configuration of an ultrasound diagnosis apparatus 1000 according to other embodiments.

According to an embodiment, the ultrasound diagnosis apparatus 1000 may include a probe 20, an ultrasound transceiver 1100, an image processor 1200, a communication module 1300, a display 1400, a memory 1500, an input device 1600, and a controller 1700. The above-mentioned components may be connected with one another via a bus 1800.

The ultrasound diagnosis apparatus 1000 may be implemented as a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits an ultrasound signal to an object 10 and receives an echo signal reflected from the object 10 in response to a driving signal applied by the ultrasound transceiver 1100. The probe 20 includes a plurality of transducers, and the plurality of transducers oscillate in response to electric signals and generate acoustic energy that is ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 1110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed by the delay times respectively correspond to a plurality of piezoelectric vibrators included in the probe 20. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 1120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In addition, the receiver 1120 may not include the amplifier 1122 according to its implemented configuration. In other words, when the sensitivity of the probe 20 is improved, or the number of bits that can be processed by the ADC 1124 is increased, the receiver 1120 may not include the amplifier 1122.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a B mode, and a motion (M) mode, but also a Doppler image representing a moving object by using a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 included in a data processor 1210 extracts B mode components from ultrasound data and processes the B mode components. An image generator 1220 may generate an ultrasound image indicating signal intensities as brightness based on the B mode components extracted by the B mode processor 1212.

Similarly, a Doppler processor 1214 included in the data processor 1210 may extract Doppler components from ultrasound data, and the image generator 1220 may generate a Doppler image representing a movement of the object 10 as colors or waveforms based on the extracted Doppler components.

The image generator 1220 may generate a three-dimensional (3D) ultrasound image of the object 10 by performing volume rendering with respect to volume data and may also generate an elastic image that shows a degree of deformation of the object 10 depending on pressure. Furthermore, the image generator 1220 may indicate various pieces of additional information in an ultrasound image by using text and graphics. In addition, the generated ultrasound image may be stored in the memory 1500.

The display 1400 displays and outputs the generated ultrasound image. The display 1400 may display not only an ultrasound image but also various pieces of information processed by the ultrasound diagnosis apparatus 1000 on a screen via a graphical user interface (GUI). In addition, the ultrasound diagnosis apparatus 1000 may include two or more displays 160 according to embodiments.

The communication module 1300 is connected to a network 31 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of the object 10, e.g., an ultrasound image, ultrasound data, and Doppler data regarding the object 10, via the network 31 and may also transmit or receive medical images captured by another medical apparatus such as a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the object 10. Furthermore, the communication module 1300 may perform data communication not only with a server or a medical apparatus in a hospital, but also with a portable terminal of a medical doctor or patient.

The communication module 1300 is connected to the network 31 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one of a base station, an external terminal, and a server on a mobile communication network. The wireless signals may be voice call signals, video call signals, or various types of data for transmission and reception of text/multimedia messages.

The memory 1500 stores various pieces of data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be implemented as various storage media such as a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which data for controlling the ultrasound diagnosis apparatus 1000 is received from a user. The input device 1600 may include a hardware configuration such as a keypad, a mouse, a touchpad, a touch screen, a track ball, and a jog switch, but is not limited thereto, and may further include various input means such as an electrocardiogram measurement module, a respiration measurement module, a voice recognition sensor, a gesture recognition sensor, a fingerprint recognition sensor, an iris recognition sensor, a depth sensor, and a distance sensor.

The controller 1700 may control all operations of the ultrasound diagnosis apparatus 1000. In other words, the controller 1700 may control operations among the probe 20, the ultrasound transceiver 1100, the image processor 1200, the communication module 1300, the memory 1500, and the input device 1600 shown in FIG. 13.

All or some of the probe 20, the ultrasound transceiver 1100, the image processor 1200, the communication module 1300, the memory 1500, the input device 1600, and the controller 1700 may be implemented as software modules. However, embodiments of the present disclosure are not limited thereto, and some of the components stated above may be implemented as hardware modules. Furthermore, at least some of the ultrasound transceiver 1100, the image processor 1200, and the communication module 1300 may be included in the controller 1700. However, embodiments of the present disclosure are not limited thereto.

Embodiments may be implemented through computer-readable recording media having recorded thereon computer-executable instructions such as program modules that are executed by a computer. The computer-readable recording media may be any available media that can be accessed by a computer and include both volatile and nonvolatile media and both detachable and non-detachable media. Furthermore, the computer-readable recording media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal such as a carrier wave, or other transmission mechanism, and may include any information transmission media.

Furthermore, in the present specification, the term "unit" may be a hardware component such as a processor or circuit and/or a software component that is executed by a hardware component such as a processor.

The above description of the present disclosure is provided for illustration, and it will be understood by those of ordinary skill in the art that various changes in form and details may be made therein without departing from essential features and the spirit and scope of the present disclosure as defined by the following claims. Accordingly, the above embodiments and all aspects thereof are examples only and are not limiting. For example, each component defined as an integrated component may be implemented in a distributed fashion. Likewise, components defined as separate components may be implemented in an integrated manner.

The invention claimed is:

1. An ultrasound diagnosis apparatus comprising:
an ultrasound probe configured to transmit an ultrasound signal to an object and receive an ultrasound echo signal returned from the object;
a controller configured to determine a velocity of the object based on the ultrasound echo signal; and
a display configured to display a spectral Doppler image showing velocities of the object over time, and to display a user interface for setting a velocity interval; interval,
wherein the controller is further configured to receive user inputs of selecting an interval within a range of the velocities of the object shown in the spectral Doppler image based on the user interface, and adjusting an output volume of an audible sound corresponding to velocities in the selected interval,
wherein the ultrasound diagnosis apparatus is configured to output, based on the adjusted output volume of the audible sound, an adjusted audible sound representing the velocities of the object over time,
wherein the controller is further configured to control the display to display an image showing a distribution of the velocities of the object in the selected interval,
wherein the image includes a graph which plots sound volume against the velocity, wherein the graph is divided into at least a first velocity interval and a second velocity interval, and wherein the graph includes a first visual element representing a first sound volume of the first velocity interval and a second visual element representing a second sound volume of the second velocity interval,
wherein the first sound volume is proportional to one of a number of times that velocities in the first velocity interval are detected, a length of time during which velocities in the first velocity interval are detected, a power of Doppler shift frequency components corresponding to velocities in the first velocity interval, and a power of audible sound corresponding to velocities in the first velocity interval, during a time period in which velocity of the object is displayed in the spectral Doppler image,
wherein the second sound volume is proportional to one of a number of times that velocities in the second velocity interval are detected, a length of time during which velocities in the second velocity interval are detected, a power of Doppler shift frequency components corresponding to velocities in the second velocity interval, and a power of audible sound corresponding to velocities in the second velocity interval, during a time period in which velocity of the object is displayed in the spectral Doppler image, and
wherein the controller is further configured to receive a first user input of selecting one of the first velocity interval and the second velocity interval and receive a second user input of adjusting a sound volume with respect to the selected one of the first velocity interval and the second velocity interval.

2. The ultrasound diagnosis apparatus of claim 1, wherein the controller is further configured to adjust the output volume of the audible sound corresponding to the velocities in the interval within the range of the velocities of the object, based on the user inputs and information about a power of a Doppler shift frequency corresponding to the interval.

3. The ultrasound diagnosis apparatus of claim 2, wherein the controller is further configured to adjust, based on the information about the power of the Doppler shift frequency, the power of the Doppler shift frequency corresponding to the interval within the range of the velocities of the object, and control the ultrasound diagnosis apparatus to output an audible sound representing velocities of the object over time by mixing the Doppler shift frequency having the adjusted power with Doppler shift frequencies corresponding to remaining intervals other than the interval within the range of the velocities of the object.

4. The ultrasound diagnosis apparatus of claim 1, wherein the controller is further configured to receive the user input of selecting the interval within the range of the velocities of the object by splitting the range of the velocities of the object shown in the spectral Doppler image into a plurality of velocity intervals and selecting one of the plurality of velocity intervals.

5. The ultrasound diagnosis apparatus of claim 1, wherein the controller is further configured to control, when the user input of adjusting the output volume of the audible sound corresponding to the velocities in the selected interval is received, the display to display an adjusted sound volume with respect to the selected interval in the image showing the distribution of the velocities of the object.

6. The ultrasound diagnosis apparatus of claim 1, wherein the controller is further configured to receive the user input of adjusting the output volume of the audible sound corresponding to the velocities in the selected interval by receiving a user input of manipulating a time gain compensation (TGC) button within a control panel included in the ultrasound diagnosis apparatus.

7. The ultrasound diagnosis apparatus of claim 1, wherein the controller is further configured to control, when the user input of selecting the interval within the range of the velocities of the object is received, the ultrasound diagnosis apparatus to output only an audible sound corresponding to the selected interval among audible sounds representing the velocities of the object over time.

8. The ultrasound diagnosis apparatus of claim 1, wherein the controller is further configured to control, when the user input of selecting the interval within the range of the velocities of the object is received, the display to display on a brightness (B) mode image of the object a color Doppler image showing only velocities in the selected interval among the velocities of the object in a certain color.

9. The ultrasound diagnosis apparatus of claim 1, wherein the controller is further configured to receive the user inputs of selecting a time interval within a time range shown in the spectral Doppler image and adjusting an output volume of an audible sound corresponding to the velocity interval within a range of velocities detected during the selected time interval.

10. A method of outputting a velocity of an object, the method comprising:
transmitting an ultrasound signal to an object and receiving an ultrasound echo signal returned from the object;
determining a velocity of the object based on the ultrasound echo signal;
displaying a spectral Doppler image showing velocities of the object over time and a user interface for setting a velocity interval;
receiving user inputs of selecting an interval within a range of the velocities of the object shown in the spectral Doppler image based on the user interface and adjusting an output volume of an audible sound corresponding to velocities in the selected interval;
outputting, based on the adjusted output volume of the audible sound, an adjusted audible sound representing the velocities of the object over time, and
displaying an image showing a distribution of the velocities of the object in the selected interval,
wherein the image includes a graph which plots sound volume against the velocity, wherein the graph is divided into at least a first velocity interval and a second velocity interval, and wherein the graph includes a first visual element representing a first sound volume of the first velocity interval and a second visual element representing a second sound volume of the second velocity interval,
wherein the first sound volume is proportional to one of a number of times that velocities in the first velocity interval are detected, a length of time during which velocities in the first velocity interval are detected, a power of Doppler shift frequency components corresponding to velocities in the first velocity interval, and a power of audible sound corresponding to velocities in the first velocity interval, during a time period in which velocity of the object is displayed in the spectral Doppler image,
wherein the second sound volume is proportional to one of a number of times that velocities in the second velocity interval are detected, a length of time during which velocities in the second velocity interval are detected, a power of Doppler shift frequency components corresponding to velocities in the second velocity interval, and a power of audible sound corresponding to velocities in the second velocity interval, during a time period in which velocity of the object is displayed in the spectral Doppler image, and
wherein the method further comprises receiving a first user input of selecting a sub velocity interval in the image and a second user input of adjusting a sound volume with respect to the sub velocity interval.

11. The method of claim 10, wherein the outputting of the audible sound representing the velocities of the object over time based on the adjusted output volume of the audible sound comprises adjusting the output volume of the audible sound corresponding to the velocities in the interval within the range of the velocities of the object, based on the user inputs and information about a power of a Doppler shift frequency corresponding to the interval.

12. The method of claim 11, wherein the outputting of the audible sound representing the velocities of the object over time based on the adjusted output volume of the audible sound comprises adjusting, based on the information about the power of the Doppler shift frequency, the power of the Doppler shift frequency corresponding to the interval within the range of the velocities of the object and outputting an audible sound representing the velocities of the object over time by mixing the Doppler shift frequency having the adjusted power with Doppler shift frequencies corresponding to remaining intervals other than the interval within the range of the velocities of the object.

13. The method of claim 10, wherein the receiving of the user input of selecting the interval within the range of the velocities of the object shown in the spectral Doppler image comprises receiving a user input of splitting the range of the velocities of the object shown in the spectral Doppler image into a plurality of velocity intervals and selecting one of the plurality of velocity intervals.

14. The method of 11, wherein the receiving of the user input of adjusting the output volume of the audible sound corresponding to the velocities in the selected interval comprises:
changing the output volume of the audible sound corresponding to the velocities in the selected interval.

* * * * *